United States Patent
Kazerooni et al.

(12)

(10) Patent No.: US 11,819,428 B2
(45) Date of Patent: *Nov. 21, 2023

(54) SEMI-ACTIVE ROBOTIC JOINT

(71) Applicant: The Regents of the University of California, Oakland, CA (US)

(72) Inventors: Homayoon Kazerooni, Berkeley, CA (US); Minerva P. Pillai, Redwood City, CA (US); Wayne Yi-Wei Tung, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/663,610

(22) Filed: May 16, 2022

(65) Prior Publication Data
US 2022/0273469 A1 Sep. 1, 2022

Related U.S. Application Data

(63) Continuation of application No. 15/631,553, filed on Jun. 23, 2017, now Pat. No. 11,369,494.
(Continued)

(51) Int. Cl.
*A61H 3/00* (2006.01)
*A61F 2/70* (2006.01)
(Continued)

(52) U.S. Cl.
CPC .................. *A61F 2/70* (2013.01); *A61F 2/64* (2013.01); *A61F 5/0125* (2013.01);
(Continued)

(58) Field of Classification Search
CPC .. A61F 2002/6854; A61F 2/604; A61F 2/605; A61F 2/64; A61F 2/6607
See application file for complete search history.

(56) References Cited

U.S. PATENT DOCUMENTS

| 7,410,472 B2 | 8/2008 | Yakimovich et al. |
| 9,730,814 B2 | 8/2017 | Omarsson et al. |

(Continued)

FOREIGN PATENT DOCUMENTS

| WO | 2010036791 A1 | 4/2010 |
| WO | 2017223442 A1 | 12/2017 |

OTHER PUBLICATIONS

U.S. Appl. No. 15/631,553, Final Rejection, dated Jun. 26, 2020, 12 pgs.
(Continued)

*Primary Examiner* — LaToya M Louis
(74) *Attorney, Agent, or Firm* — Sterne, Kessler, Goldstein & Fox P.L.L.C.

(57) ABSTRACT

A robotic joint comprises a first link, a middle link, a torque generator, a second link, and a locking mechanism. Different ends of the middle link are rotatably coupled to the first link and the second link. The torque generator is coupled to the first link and the middle link and is configured to produce torque between these links. The locking mechanism is switchable between a locking state and an unlocking state. In the unlocking state, the locking mechanism allows free rotation of the second link relative to the middle link in the first and second rotation directions. In the locking state, the locking mechanism is configured to impede rotation of the second link relative to the middle link in the first rotation direction and to allow rotation of the second link relative to the middle link in the second rotation direction opposite of the first rotation direction.

19 Claims, 27 Drawing Sheets

Related U.S. Application Data

(60) Provisional application No. 62/354,263, filed on Jun. 24, 2016.

(51) Int. Cl.
| | |
|---|---|
| *B25J 17/00* | (2006.01) |
| *A61F 2/64* | (2006.01) |
| *A61F 5/01* | (2006.01) |
| *B25J 9/00* | (2006.01) |
| *B25J 9/10* | (2006.01) |
| *A61F 2/68* | (2006.01) |
| *A61F 2/50* | (2006.01) |
| *A61F 2/76* | (2006.01) |
| *A61F 2/74* | (2006.01) |

(52) U.S. Cl.
CPC .............. *A61F 5/0127* (2013.01); *A61H 3/00* (2013.01); *B25J 9/0006* (2013.01); *B25J 9/106* (2013.01); *B25J 17/00* (2013.01); *A61F 2/74* (2021.08); *A61F 2002/5006* (2013.01); *A61F 2002/5073* (2013.01); *A61F 2002/6854* (2013.01); *A61F 2002/701* (2013.01); *A61F 2002/704* (2013.01); *A61F 2002/764* (2013.01); *A61F 2002/7625* (2013.01); *A61F 2002/7645* (2013.01); *A61F 2005/0155* (2013.01); *A61F 2005/0158* (2013.01); *A61F 2005/0169* (2013.01); *A61H 2205/102* (2013.01)

(56) References Cited

U.S. PATENT DOCUMENTS

| | | |
|---|---|---|
| 9,844,448 B2 | 12/2017 | Karlsson et al. |
| 2003/0062241 A1 | 4/2003 | Irby et al. |
| 2005/0251079 A1 | 11/2005 | Carvey et al. |
| 2006/0206043 A1 | 9/2006 | Yakimovich et al. |
| 2007/0123997 A1 | 5/2007 | Herr et al. |
| 2015/0134078 A1 | 5/2015 | Amundson et al. |
| 2015/0272765 A1 | 10/2015 | Gilbert et al. |
| 2015/0328017 A1 | 11/2015 | Langenfeld et al. |
| 2016/0287423 A1 | 10/2016 | Ramirez |
| 2017/0367852 A1 | 12/2017 | Kazerooni et al. |

OTHER PUBLICATIONS

U.S. Appl. No. 15/631,553, Examiner Interview Summary dated Feb. 14, 2022, 1 page.
U.S. Appl. No. 15/631,553, Final Office Action dated Feb. 8, 2019, 12 pgs.
U.S. Appl. No. 15/631,553, Non Final Office Action dated Jun. 15, 2018, 14 pgs.
U.S. Appl. No. 15/631,553, Non-Final Office Action dated Apr. 15, 2021, 15 pgs.
U.S. Appl. No. 15/631,553, Notice of Allowance dated Feb. 14, 2022, 15 pgs.
U.S. Appl. No. 15/631,553, Restriction Requirement dated Jan. 3, 2018, 6 pgs.
Int'l Application Serial No. PCT/US17/38987, Int'l Search Report and Written Opinion dated Oct. 3, 2017, 12 pgs.
Int'l Application Serial No. PCT?US17/38987, Int'l Preliminary Report on Patentability dated Jan. 3, 2019, 8 pgs.

SEMI-ACTIVE ROBOTIC JOINT

CROSS-REFERENCE TO RELATED APPLICATIONS

This application is a continuation of U.S. patent application Ser. No. 15/631,553, filed Jun. 23, 2017, which claims the benefit of U.S. Provisional Patent Application No. 62/354,263, filed Jun. 24, 2016. Both of these applications are incorporated herein by reference in their entireties and for all purposes along with all other references cited in this application.

TECHNICAL FIELD

The apparatus described is an energetically passive exoskeleton knee, configured to be incorporated into an exoskeleton leg.

BACKGROUND

Lower extremity exoskeleton technology has been geared towards benefiting medical and augmentation fields. Functional modularity in exoskeleton design allows practitioners to prescribe exoskeletons, which can be geared towards the wearer's needs and abilities. While most modular knee exoskeleton technology either lives in the realm of medicine or augmentation, a stance assistive knee exoskeleton can benefit both able-bodied individuals as well as individuals with decreased quadriceps function or knee weakness.

Fully passive systems are lower cost but have limited functionality. Powered systems have diverse functionality but are expensive and large. Microcontroller controlled resistive knees are more functionally diverse than a fully passive system, but only provide system impedance to motion and can be expensive.

Passive microcontroller controlled systems can lead to a low cost and functionally versatile system. By embedding some of the required functionality into the mechanical hardware of the system, the burden on the microcontrollers and the need for sensors is reduced.

SUMMARY

Several embodiments of energetically passive robotic joints are addressed here. These energetically passive joints can be used in various exoskeletons, orthotic systems, prosthetic devices, and robotic walking machines. These embodiments do not use any external power that can be used for locomotion energy, although a battery may be used to power a micro-computer and associated sensors for computation and control. These energetically passive robotic joints, in addition to other behaviors, exhibit two useful characteristics needed to create locomotion: 1) they can exhibit appropriate resistance in response to flexion when needed while the extension is free at all times even when the joint is under the load (e. g. stance phase of an exoskeleton knee joint); and 2) they can exhibit free flexion and extension when needed (e.g. swing phase of an exoskeleton knee joint). Switching between these two states can provide the fundamental characteristic needed for locomotion. The basic behavior of these energetically passive robotic joints is described using abstract forms of electromechanical components. Then engineered embodiments are described to show how these energetically passive robotic joints are designed and built as an artificial knee for exoskeletons, orthotic systems, prosthetic devices, and robotic walking machines. Finally, several embodiments are described to teach the use of these energetically passive robotic joints for exoskeleton orthotic legs.

DETAILED DESCRIPTION

In the following description, numerous specific details are set forth in order to provide a thorough understanding of the presented concepts. The presented concepts may be practiced without some or any of these specific details. In other instances, well-known process operations have not been described in detail so as not to obscure unnecessarily the described concepts. While some concepts will be described in conjunction with the specific embodiments, it will be understood that these embodiments are not intended to be limiting.

Figure 1:
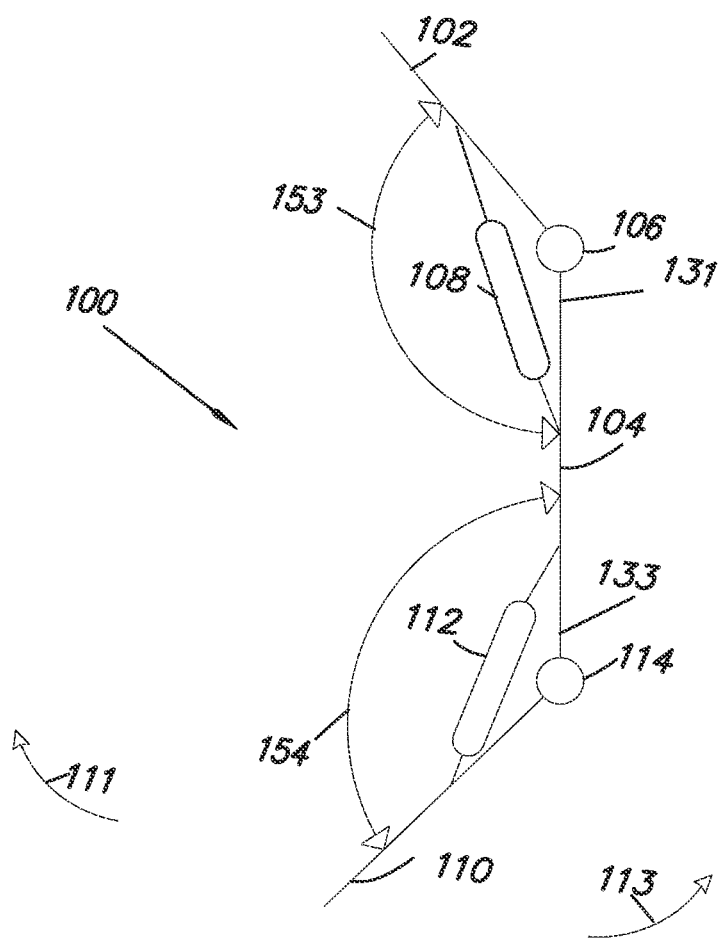
FIG. 1 illustrates a schematic representation of an embodiment of the energetically passive robotic joint.

FIG. 1 shows an embodiment of energetically passive robotic joint 100. Robotic joint 100 comprises first link 102, middle link 104, torque generator 108, second link 110, and locking mechanism 112. Middle link 104 is rotatably coupled to first link 102 from its first end 131 where first joint 106 represents the rotation of middle link 104 relative to first link 102. Torque generator 108 is capable of producing torque between first link 102 and middle link 104. Second link 110 is rotatably coupled to second end 133 of middle link 104 where second joint 114 represents the rotation of middle link 104 relative to second link 110. Locking mechanism 112 is capable of impeding the rotational motion of second link 110 with respect to middle link 104 when second link 110 is flexing relative to middle link 104. In other words, when locking mechanism 112 is in its locking state, angle 154 cannot get smaller easily and, in the limit, depending on the nature of locking mechanism 112, angle 154 cannot get smaller at all. In an embodiment of the disclosure, when locking mechanism 112 is in its locking state, angle 154 cannot get smaller easily and, in the limit, depending on the nature of locking mechanism 112, angle 154 cannot get smaller at all, but can always get larger. In other words, in some embodiments of the disclosure, when locking mechanism 112 is in its locking state, middle link 104 and second link 110 get locked to each other such that angle 154 does not get smaller but can always get larger. When locking mechanism 112 is in its unlocking state, middle link 104 and second link 110 can always rotate relative to each other and angle 154 can always get larger or smaller.

For better understanding of the concept of FIG. 1, assume first link 102 is the thigh link and second link 110 is the shank link of an exoskeleton orthotic system. Further assume middle link 104 has a very short length. First direction 111 and second direction 113 represent the rotational motion of second link 110 relative to first link 102. A decrease in angle 153 or a decrease in angle 154 results in rotation of second link 110 relative to first link 102 in first direction 111. An increase in angle 153 or an increase in angle 154 results in rotation of second link 110 relative to first link 102 along second direction 113. Middle link 104 and first link 102 are flexing relative to each other, when angle 153 is getting smaller. When angle 153 is getting larger, middle link 104 and first link 102 are extending relative to each other. When angle 154 is getting smaller, second link 110 and middle link 104 are flexing relative to each other. When angle 154 is getting larger, second link 110 and middle link 104 are extending relative to each other. When second link 110 is moving along first direction 111, we mean second link 110 is flexing relative to first link 102. When second link 110 is moving along second direction 113, we mean second link 110 is extending relative to first link 102. Thus, in some embodiments, in the locking state, locking mechanism 112 is configured to impede the rotation of second link 110 relative to first link 102 in first rotation direction 111. In some embodiments, in the unlocking state, locking mechanism 112 allows free rotation of the second link 110 relative to first link 102 in first direction 111 and second direction 113. "Free rotation" is defined as motion only impeded by residual friction forces.

In some embodiments, second link 110 can always extend relative to middle link 104 along second direction 113 regardless of the state of locking mechanism 112. This means angle 154 can always become larger regardless of the state of the locking mechanism 112. However, locking mechanism 112 can impede only the flexion motion of second link 110 relative to middle link 104 when locking mechanism 112 is in its locking state. This means locking mechanism 112 can substantially impede angle 154 to become smaller when locking mechanism 112 is in its locking state. The level of this impedance to flexion of the locking mechanism 112 may vary. In some embodiments of the disclosure, locking mechanism 112 can totally lock second link 110 and middle link 104 to prevent the rotational flexion of second link 110 relative to middle link 104, when locking mechanism 112 is in its locking state. However, second link 110 and middle link 104 can extend relative to each other regardless if locking mechanism 112 is in locking state or unlocking state. The embodiment shown in FIG. 1 has novel properties which are described below.

In the preferred embodiment, in operation when locking mechanism 112 is in its locking state, second link 110 gets locked to middle link 104. In this case second link 110 and middle link 104 act as one rigid body and cannot flex relative to each other. However, both middle link 104 and second link 110 can extend relative to each other at all times. Once locking mechanism 112 prevents the flexion of second link 110 and middle link 104 relative to each other, rotational motion of middle link 104 and second link 110 taken as a whole relative to first link 102 is resisted by torque generator 108 along first direction 111. In other words, middle link 104 and second link 110, taken together, is not free to flex relative to first link 102 along first direction 111. However, second link 110 is free to rotate along second direction 113 (i.e. second link 110 can extend relative to first link 102 at all times.) When locking mechanism 112 is in an unlocked state, second link 110 rotates freely relative to first link 102 along both directions shown by first direction 111 and second direction 113. That is, the embodiment described here allows for either free motion or resisted motion of second link 110 relative to first link 102 along first direction 111 depending on the state of the locking mechanism 112. When the locking mechanism 112 is in a locking state, torque generator 108 provides resistance to flexion motion between first link 102 and second link 110 however unimpeded motion is always allowed between first link 102 and second link 110. When locking mechanism 112 is unlocked state, there will be no resistance in flexion and extension motion between first link 102 and second link 110. The importance of this is further described below.

Figure 2:
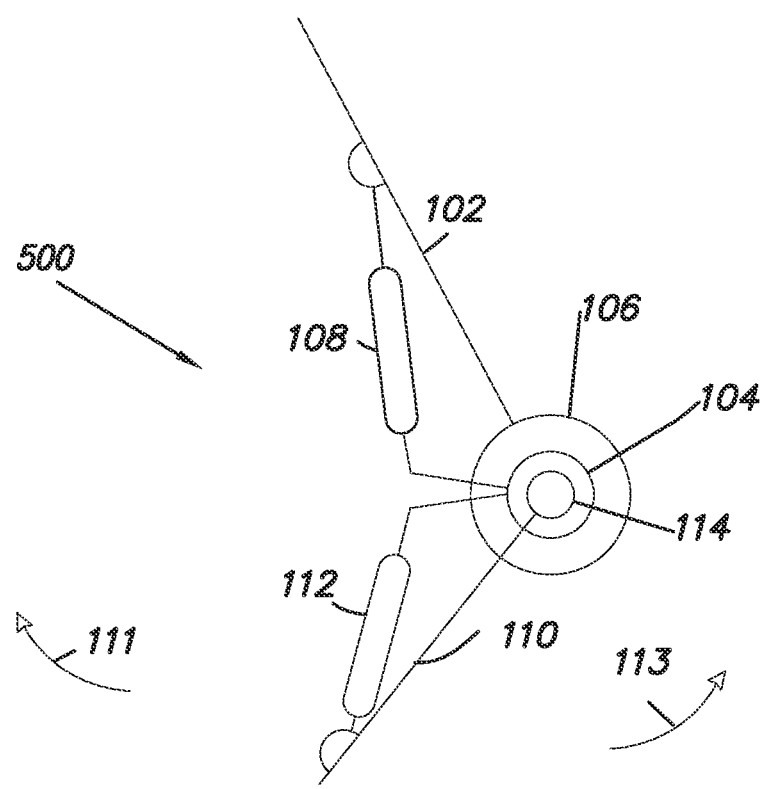
FIG. 2 is a schematic illustration of an embodiment of the disclosure.
Figure 3:
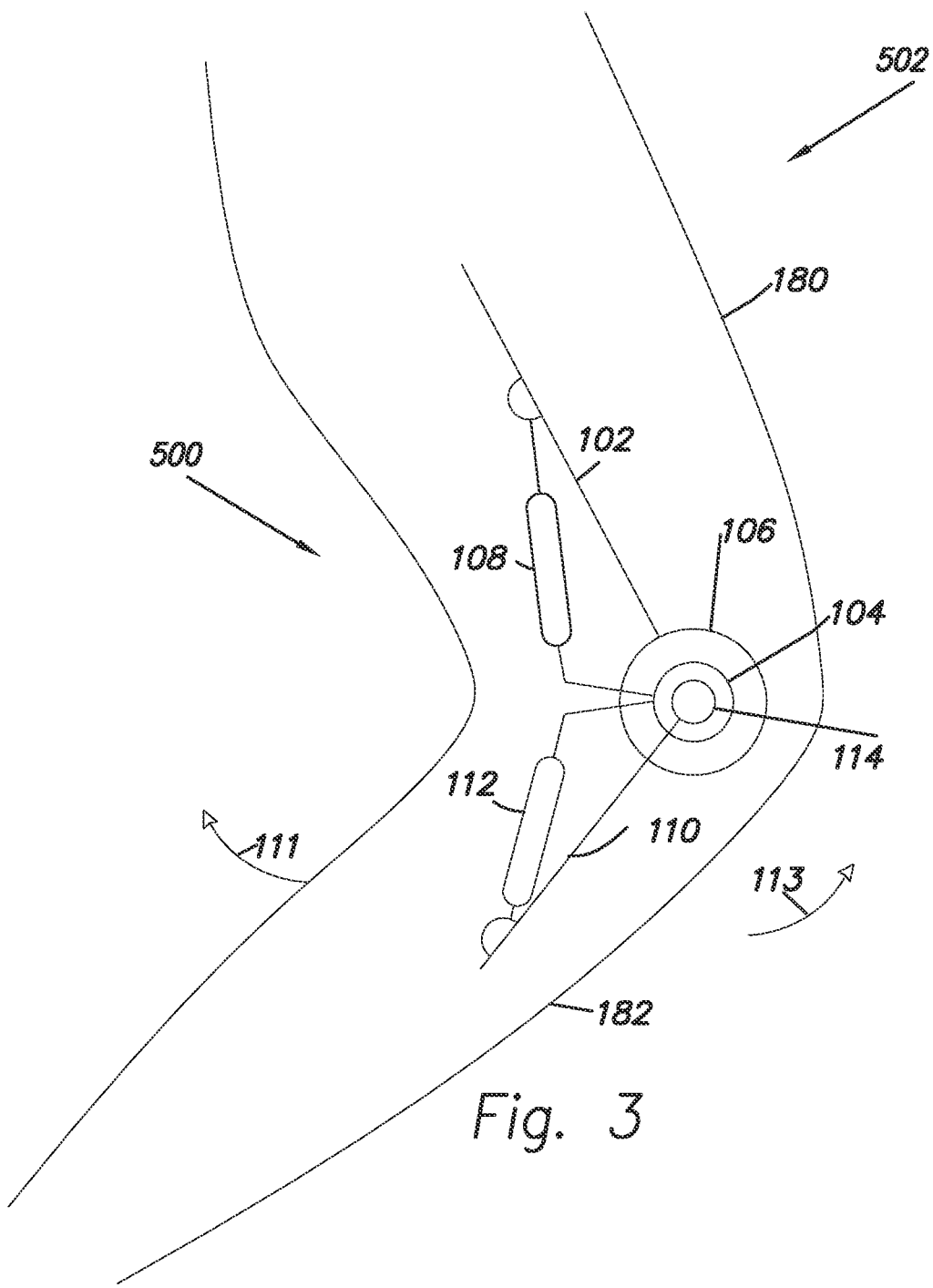
FIG. 3 is a schematic illustration of an energetically passive robotic joint worn on a person lower limb.

In some embodiments of the disclosure, the axis of rotation of first link 102 relative to middle link 104 and the axis of rotation of second link 110 relative to middle link 104 are substantially parallel to each other. In some embodiments of the disclosure, the axis of rotation of first link 102 relative to middle link 104 and the axis of rotation of second link 110 relative to middle link 104 coincide on each other. This leads to a zero length for middle link 104. FIG. 2 shows an embodiment of robotic joint 500 where middle link 104 has a zero length. Since the length of middle link 104 is shortened to zero, both joints 106 and 114 coincide with each other. This architecture is of particular importance since it leads to a smaller robotic joint. The embodiment shown in FIG. 2 has a great application as the knee joint of an exoskeleton orthotic leg that is worn by a person. This is shown in FIG. 3 where robotic joint 500 is worn on the person lower limb 502. When locking mechanism 112 is in locking state, middle link 104 gets locked to second link 110. This causes the rotation of second link 110 relative to first link 102 to be impeded by torque generator 108 along first direction 111. However, second link 110 and first link 102 can extend relative to each other because second link 110 and middle link 104 are free to extend at all times (locking mechanism 112 locks second link 110 and middle link 104 together only when they flex relative to each other). This represents the stance phase for robotic joint 500 where the motion of second link 110 (coupled to person's shank 182) relative to first link 102 (coupled to person's thigh 180) is impeded during knee flexion, but is free to extend. When locking mechanism 112 is in unlocking state, the rotation of second link 110 relative to first link 102 is free in both directions 111 and 113. This represents the swing phase for robotic joint 500 where person's shank 182 is free to move relative to person's thigh 180 in both flexion and extension rotations. In summary, the robotic joint shown in FIG. 3 is able to successfully duplicate the properties that are needed for an orthotic or a prosthetic leg. Just before the stance phase is over, locking mechanism 112 unlocks middle link 104 from second link 110. This causes free motion of second link 110 relative to middle link 104 for flexion and extension needed during the swing phase. Just before the leg strikes the ground, locking mechanism 112 moves to locking state where second link 110 cannot move toward middle link 104 anymore (i.e. second link 110 cannot flex relative middle link 104.) When locking mechanism 112 is in its locking state, the extension of second link 110 relative to middle link 104 is possible. This means the person wearing robotic joint 500 can always extend regardless of status of locking mechanism 112.

As shown in FIG. 3, in some embodiments of the disclosure, first link 102 is configurable to move in unison with person's thigh 180 and second link 110 is configurable to move in unison with person's shank 182. In some embodiments of the disclosure, first link 102 is configurable to be coupled to person's thigh 180 and second link 110 is configurable to be coupled to person's shank 182. As described below various braces can be used to allow for this coupling. One can use robotic joint 500 in reverse position; this means in some embodiments of the disclosure, first link 102 is configurable to move in unison with person's shank 182 and second link 110 is configurable to move in unison with person's thigh 180. In some embodiments of the disclosure, first link 102 is configurable to be coupled to person's shank 182 and second link 110 is configurable to be coupled to said person's thigh 180. Various braces can be used to allow for this coupling. In some embodiments, these braces may take the form of straps, rigid connections, semi-rigid connections or combinations of these elements.

In some embodiments of the disclosure, torque generator 108 may produce a passive resistive torque between first link 102 and middle link 104. In these embodiments of the disclosure, torque generator 108 does not require any external energy source to deliver movement. In this case, one can imagine torque generator 108 as a simple spring that resists external flexion torques (e.g. torque imposed by the wearer) that attempt to flex first link 102 and middle link 104 relative to each. In these embodiments, torque generator 108 represents the general mechanism that generates passive resistive torques. Examples of the torque generator 108 include without limitation a pneumatic or hydraulic cylinder or a cylinder with hydraulic and pneumatic components, gas springs, hydraulic dampers, lockable gas springs, and lockable dampers. In some embodiments of the disclosure, the torque generator 108 is capable of locking, such that the locked torque generator resists all motion of the first link 102 relative to the middle link 104. In these embodiments, an actuator can be present to unlock the torque generator. In some embodiments of the disclosure, the actuator for the lockable torque generator 108 comprises an element or combination of elements selected from a group consisting of electric motors, electric motors with transmission, solenoids, hydraulic actuators, and pneumatic actuators.

In some embodiments of the disclosure, torque generator 108 is an active element that can produce arbitrary torque between first link 102 and middle link 104. In this case, one can imagine torque generator 108 as an actuator that provides flexion and extension torques between first link 102 and middle link 104 regardless of external torques. In these embodiments of the disclosure, electric motors and actuators are used to provide controllable torque at the torque generator 108. This allows the torque profile of torque generator 108 to be customized for various tasks. For instance, walking and stair ascent require different torque profiles at the person's knee.

Figure 4:
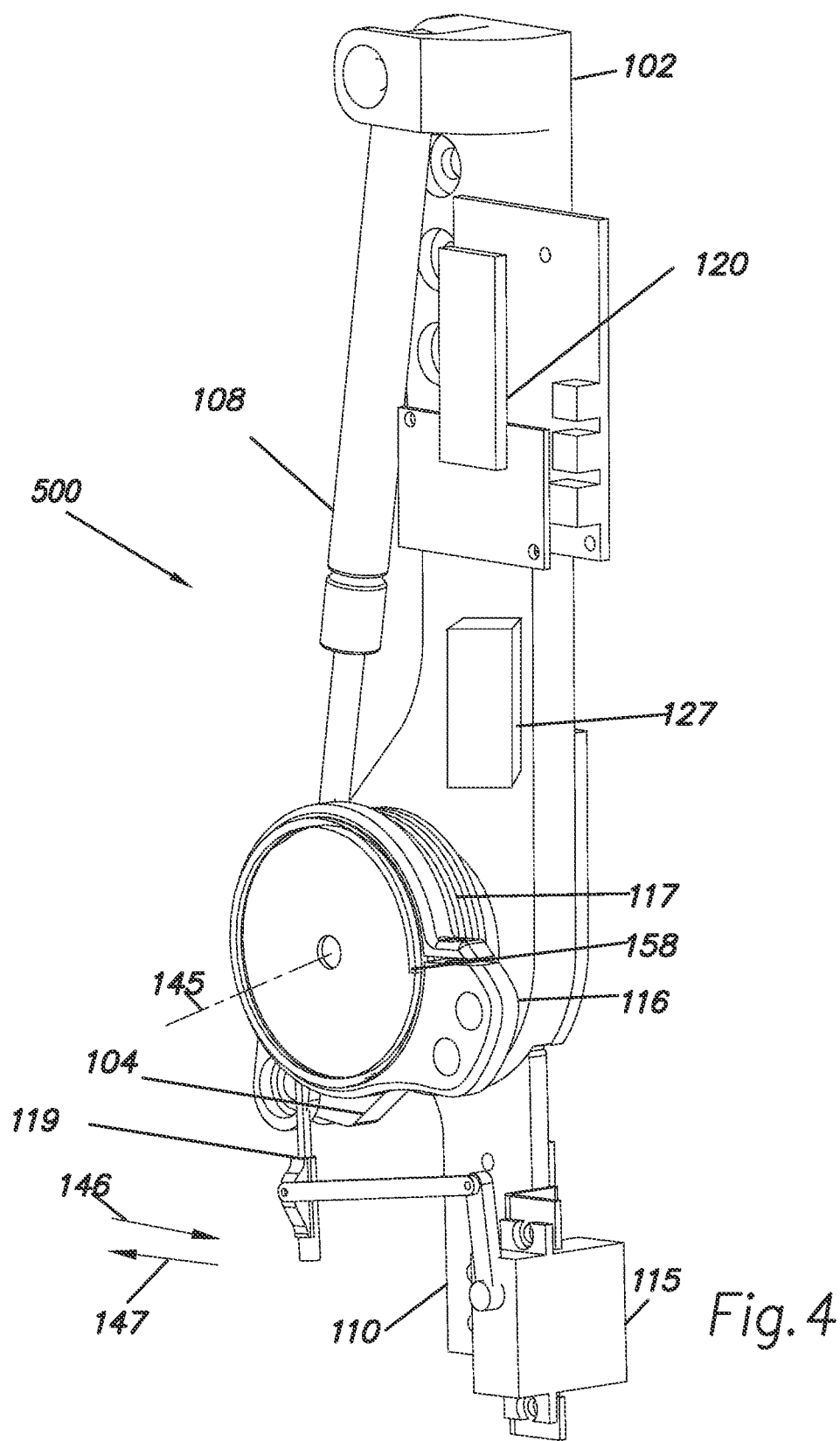
FIG. 4 represents an embodiment of the energetically passive robotic joint.
Figure 5:
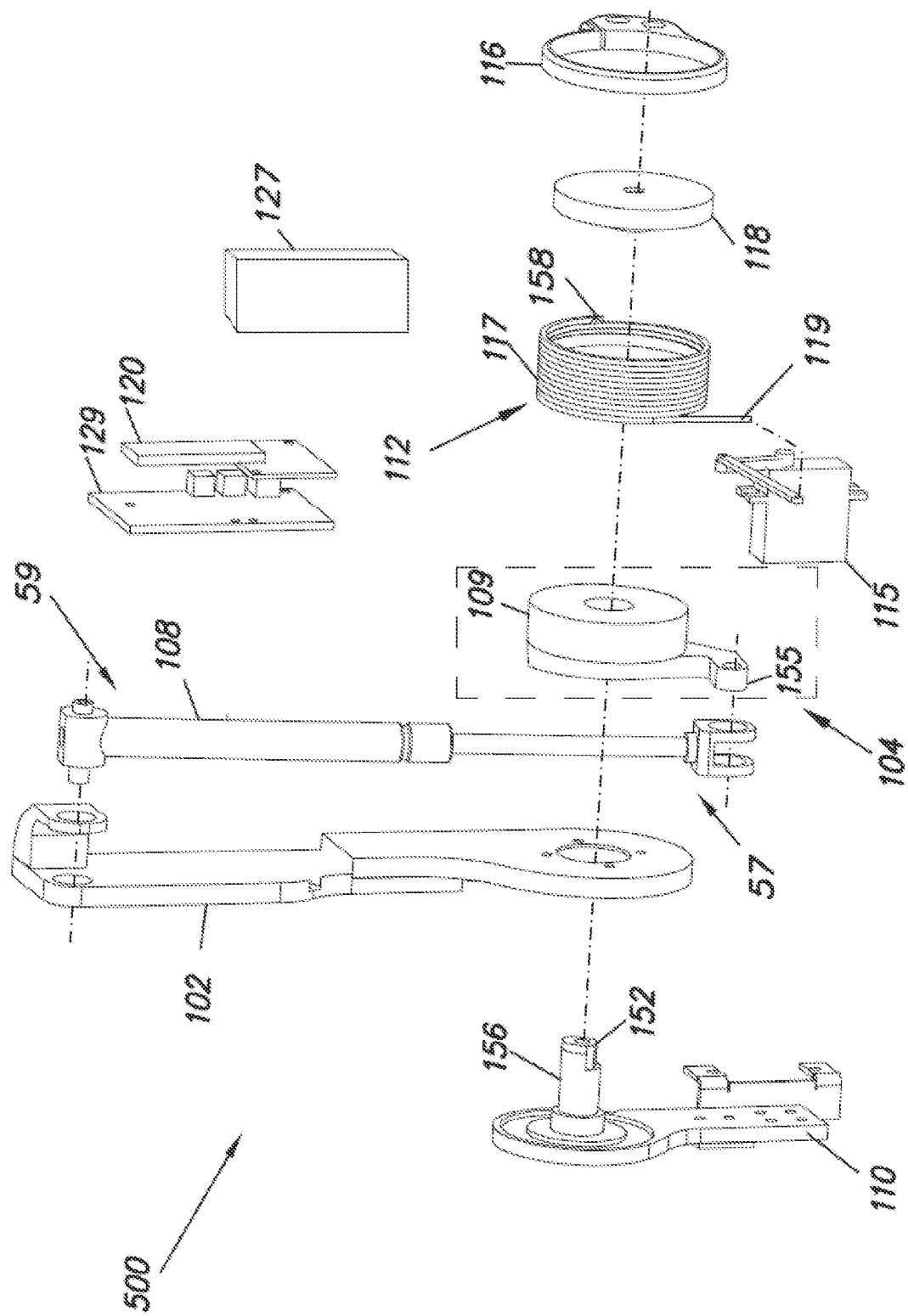
FIG. 5 is an exploded view of the embodiment shown in FIG. 4.

FIG. 4 shows an embodiment of robotic joint 500 which is designed based on the operation of embodiments described above and depicted in FIG. 1, FIG. 2, and FIG. 3. FIG. 5 shows an exploded view of robotic joint 500 shown in FIG. 4. In this embodiment, first joint 106 and second joint 114 coincide on each other and therefore middle link 104 has zero length. With the help of FIGS. 4 through 8, robotic joint 500 is described below. The embodiment of robotic joint 500 comprises a first link 102 and a middle link 104 which is rotatably coupled to first link 102. Middle link 104 has zero length whereas the length is the distance between joint 106 and second joint 114, as shown in FIG. 5. Robotic joint 500 further comprises a torque generator 108 which is capable of producing a resistive torque between first link 102 and middle link 104. Middle link 104, as shown in FIG. 5, comprises an arm 155 and arbor 109. Torque generator 108 is rotatably coupled to arm 155 (a component of middle link 104) from its first end 57. Torque generator 108 is rotatably coupled to first link 102 from its second end 59. In some embodiments of the disclosure, torque generator 108 is a gas spring. In some embodiments of the disclosure, torque generator 108 is a compression coil spring. In some embodiments of the disclosure, first link 102 comprises a clevis 159 (shown in FIG. 7 and FIG. 8). Clevis 159 can be manufactured as a part of first link 102. The second end of torque generator 108 (shown by 59) is rotatably coupled to first link 102 at clevis 159. FIG. 5 also shows controller 120 on circuit board 129 and battery 127.

Figure 6:
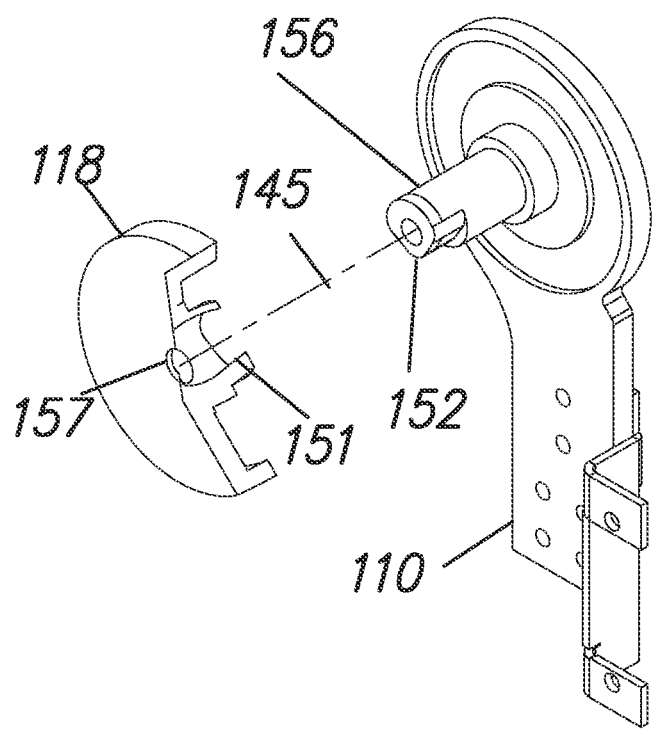
FIG. 6 is an exploded view of a portion of the embodiment shown in FIG. 4.
Figure 7:
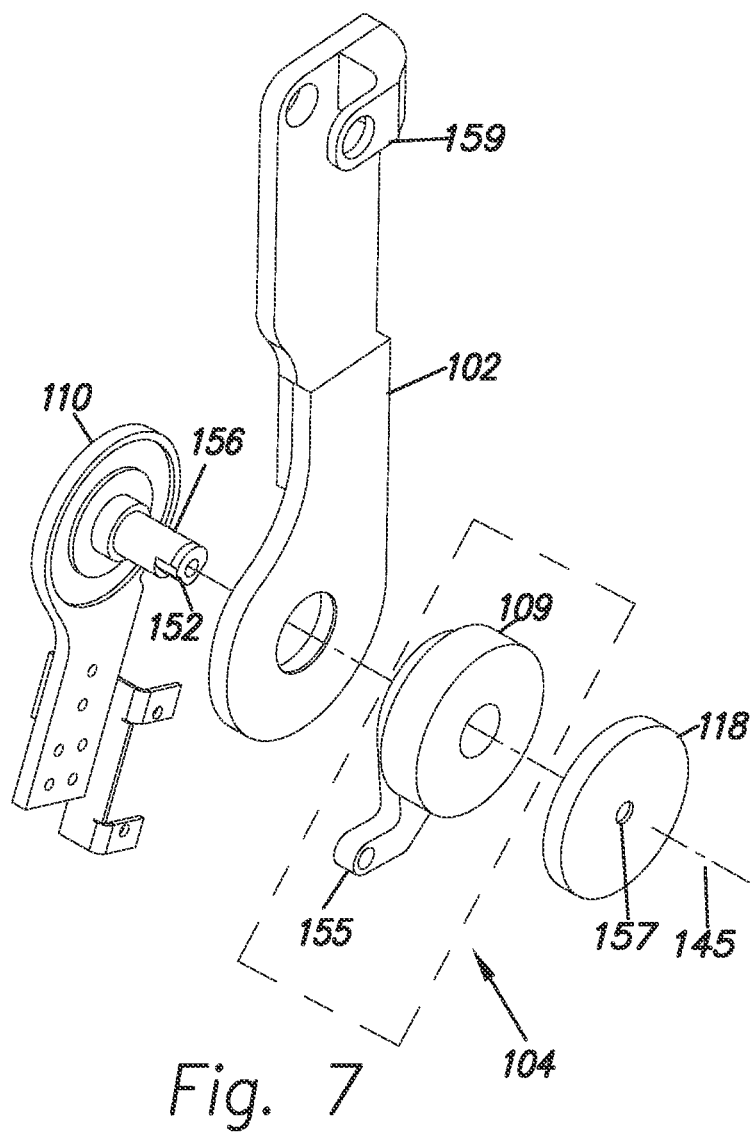
FIG. 7 is an exploded view of a portion of the embodiment shown in FIG. 4.

Robotic joint 500 further comprises a second link 110 which is rotatably coupled to middle link 104. In some embodiments of the disclosure, second link 110 comprises a main shaft 156. The coupling between second link 110 and disk 118 is achieved by interfacing a non-circular male boss 152 (shown in FIG. 6) on main shaft 156 to a corresponding non-circular female cutout 151 on disk 118 and a fastener (not shown) through hole 157. Disk 118 in FIG. 6 is shown as a section view for clarity. According to this architecture, as shown in FIG. 6, disk 118 and second link 110 are coupled to each other and rotate at the same speed.

In the absence of torque generator 108 and locking mechanism 112, first link 102, second link 110 and middle link 104 rotate independently along axis 145 of main shaft 156. A fastener (not shown in FIG. 7) through hole 157 retains the assembly containing second link 110, first link 102 and middle link 104 together. Also, note that all rotating bearings among these joints are eliminated for clarity. An ordinary skilled in the art would understand that there must be bearing surfaces (e.g., ball bearings, or roller bearings)

between second link 110, middle link 104, and first link 102 for smooth rotational motion.

Figure 8:
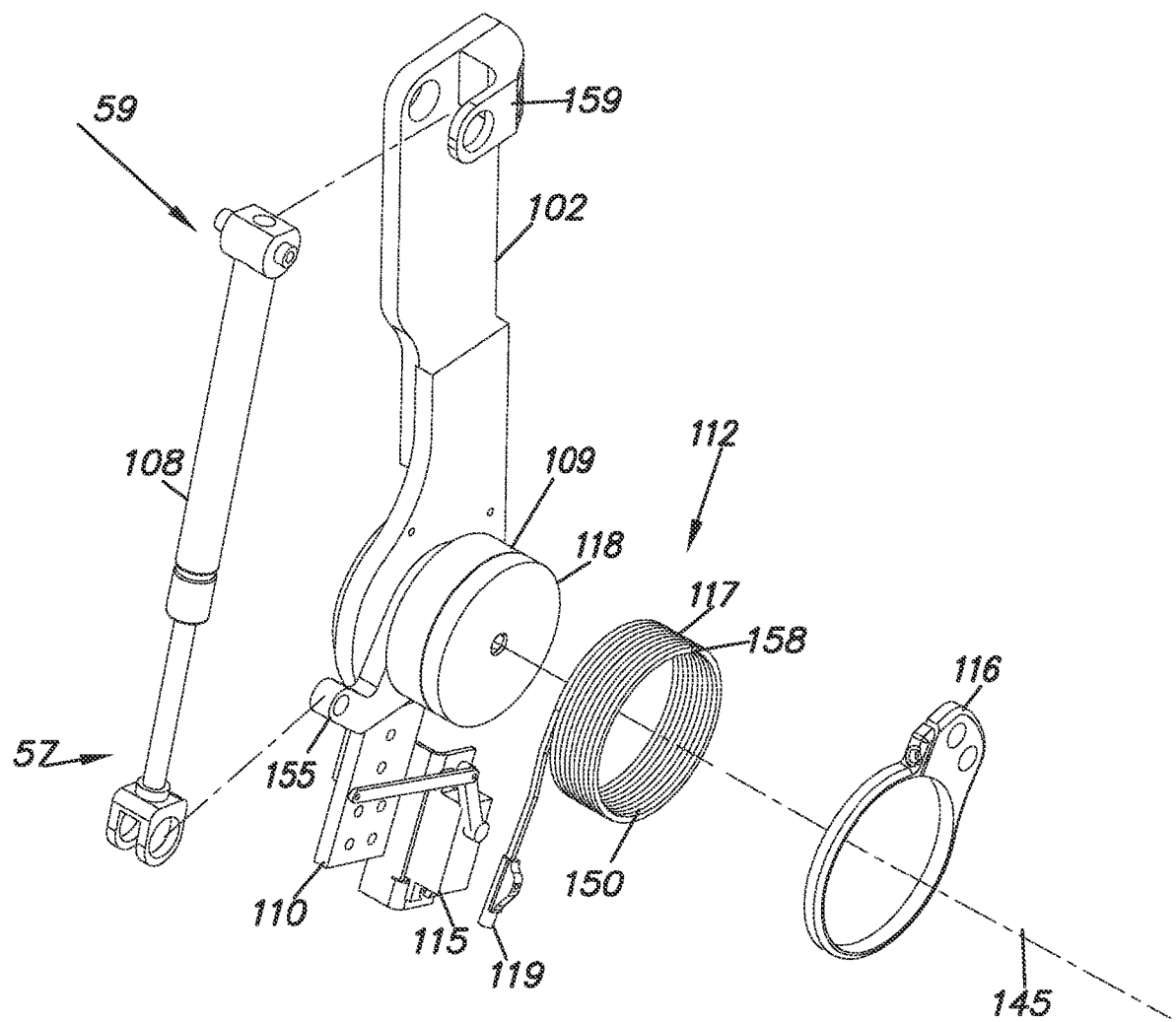
FIG. 8 is an exploded view of a portion of the embodiment shown in FIG. 4.

Locking mechanism 112, shown in FIG. 8 comprises wrap spring 117, disk 118, and actuator 115. First end 158 of wrap spring 117 is coupled to second link 110. This coupling can be accomplished by a variety of mechanical methods; however, an embodiment of this coupling is described below with the help of FIG. 8. The coupling of the wrap spring 117 to second link 110 is facilitated by using disk 118 and clamp 116. First end 158 of the warp spring 117 is mounted around disk 118. Clamp 116 clamps first end 158 of wrap spring 117 to disk 118. In some embodiments of the disclosure, clamp 116 may clamp one or more coils of the wrap spring 117 to disk 118. As described above and shown in FIG. 7, disk 118 and second link 110 are coupled to each other and rotate at the same speed. The coupling between second link 110 and disk 118 is achieved by interfacing a non-circular male boss 152 (shown in FIG. 6) on second link 110 to a corresponding non-circular female cutout 151 on disk 118 and a fastener (not shown) through hole 157. The second end 119 of wrap spring 117 is wrapped around the cylindrical surface of arbor 109 of middle link 104 such that the cylindrical surface of arbor 109 is located substantially inside wrap spring 117 with its major axis substantially parallel to the major axis 145 of wrap spring 117. Locking mechanism 112 further comprises an actuator 115 which is coupled to second link 110. Actuator 115 is capable of moving the second end 119 of the wrap spring 117 to provide pressure between the cylindrical surface of arbor 109 of middle link 104 and an inner surface 150 of wrap spring 117. This pressure causes a resistive torque between the cylindrical surface of arbor 109 and wrap spring 117. Consequently, the resistive torque between middle link 104 and second link 110 can be controlled by controlling the second end 119 of wrap spring 117. Note that disk 118 is coupled to second link 110 (they rotate together) and first end of wrap spring 117 is coupled to disk 118. As the second end 119 moves with the help of actuator 115 along arrow 146 (FIG. 9), the resistive torque between middle link 104 and second link 110 increases. As second end 119 moves with the help of actuator 115 along arrow 147 (FIG. 11), the resistive torque between middle link 104 and second link 110 decreases substantially.

Figure 9:
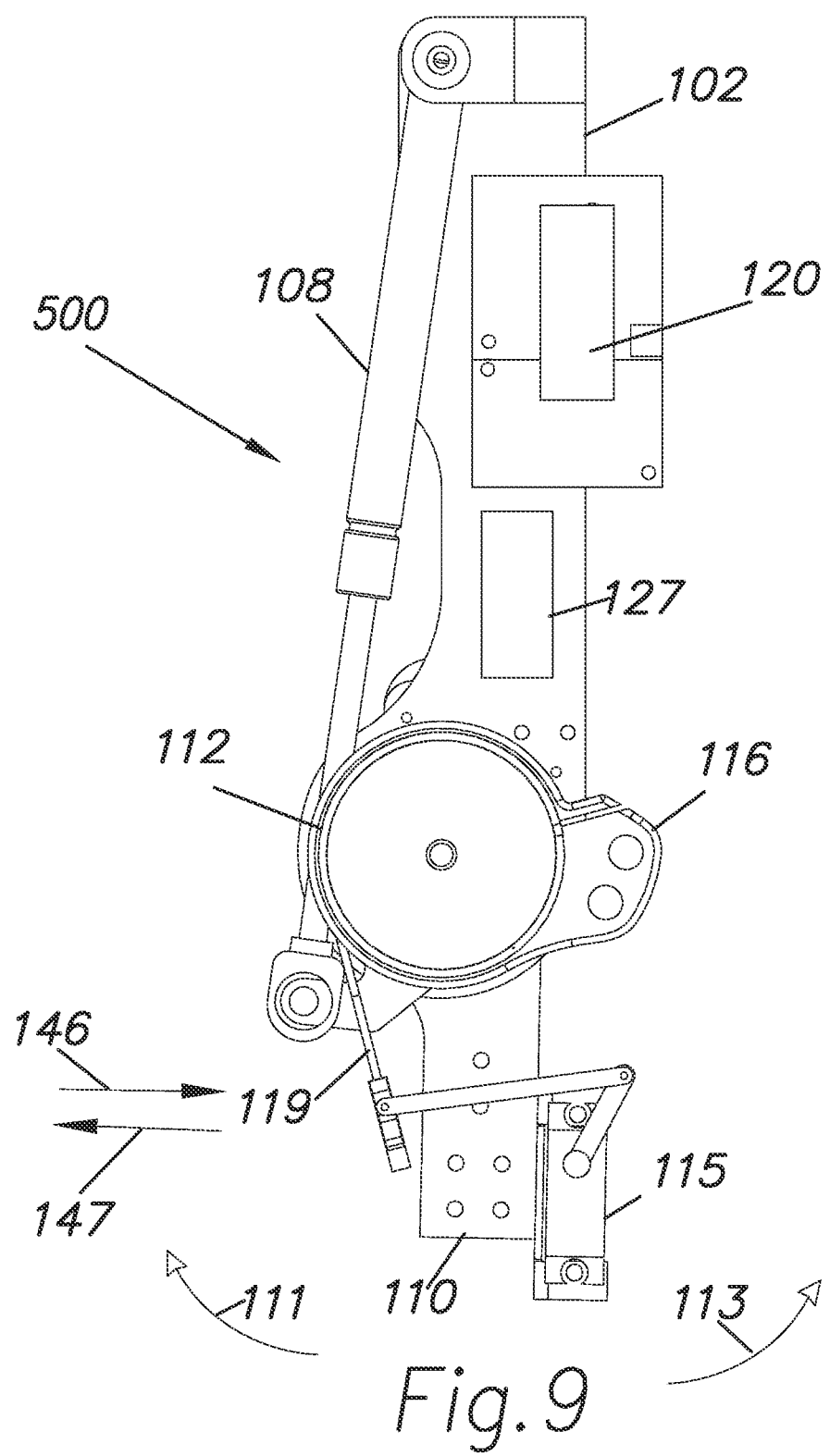
FIG. 9 illustrates an embodiment in which the locking mechanism is in a locking state.
Figure 10:
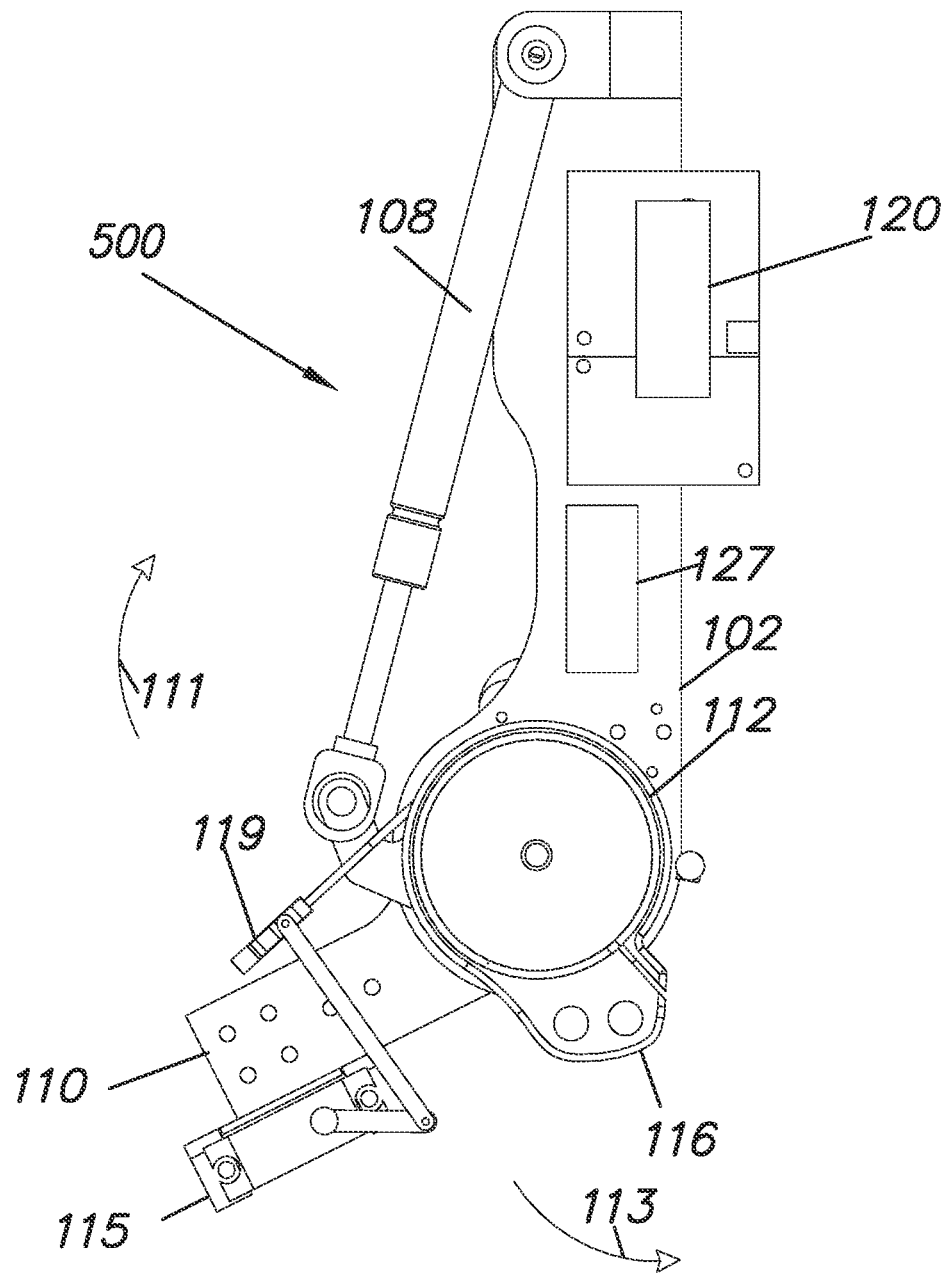
FIG. 10 illustrates an embodiment in which the locking mechanism is in a locking state.
Figure 11:
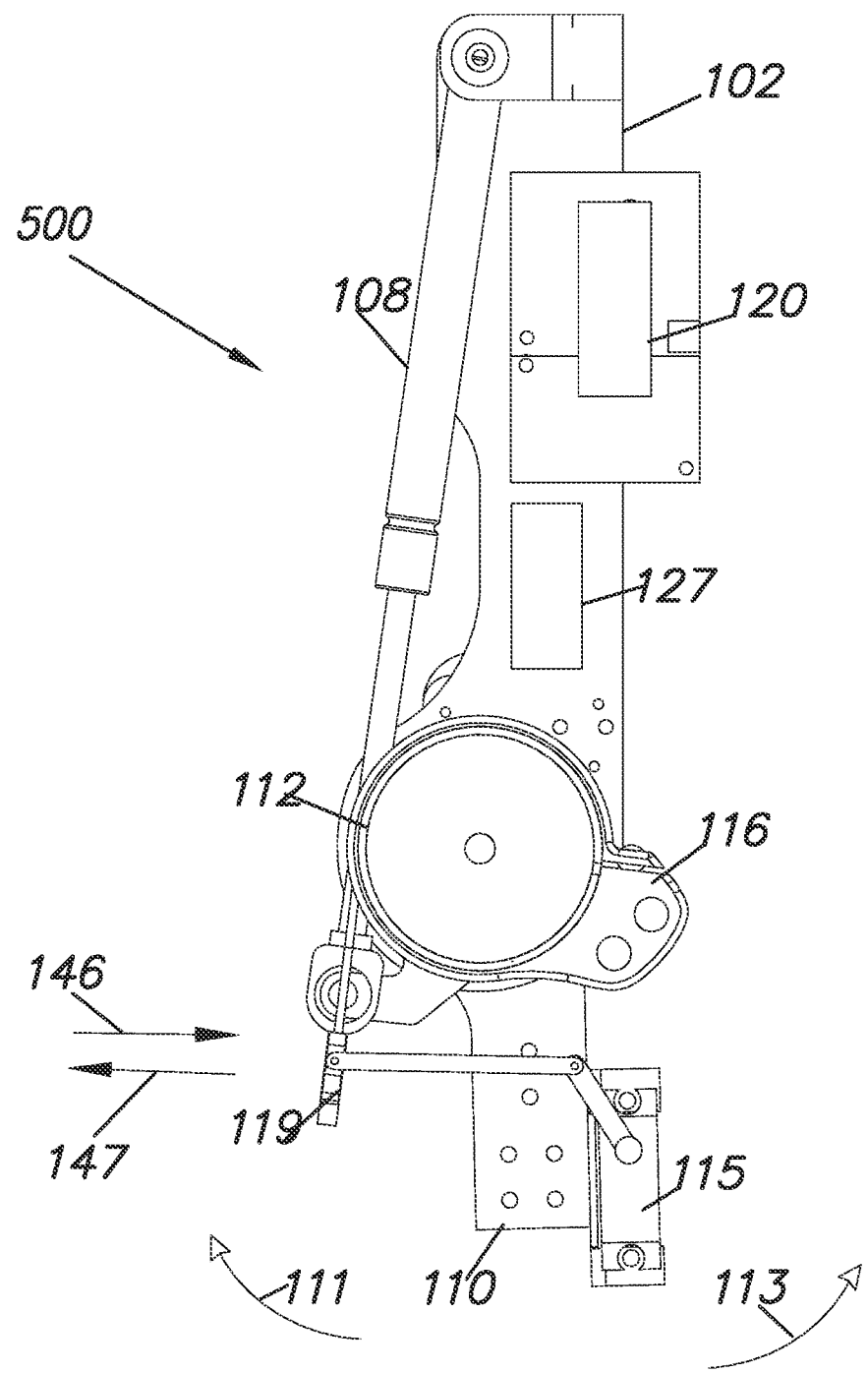
FIG. 11 illustrates an embodiment in which the locking mechanism is in an unlocking state.
Figure 12:
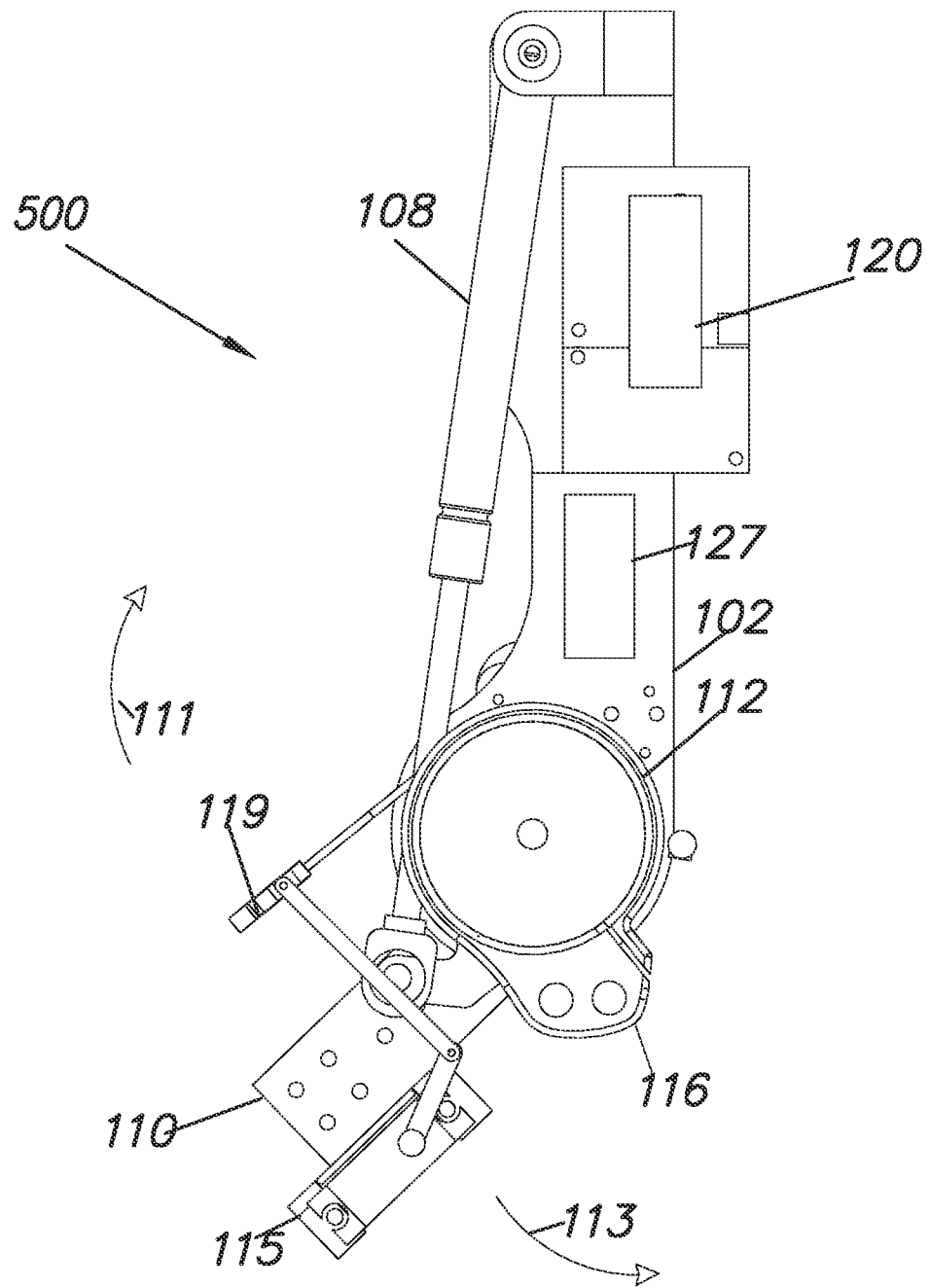
FIG. 12 illustrates an embodiment in which the locking mechanism is in an unlocking state.

FIG. 9 and FIG. 10 show an embodiment of the disclosure where torque generator 108 takes the form of a gas spring. If actuator 115 moves the second end 119 along arrow 146, locking mechanism 112 is in the locking state. In this locking state, second link 110 and middle link 104 are locked to each other and cannot flex relative to each other. In this state, the motion of second link 110 relative to first link 102 along first direction 111 occurs by compressing the gas spring torque generator 108. The compression of torque generator 108 is seen in FIG. 10. In other words, when actuator 115 moves second end 119 along arrow 146, there will be resistance for flexion of first link 102 and second link 110 relative to each other. However, first link 102 and second link 110 are free to extend relative to each other at all times even when second end 119 has been moved along arrow 146. If actuator 115 moves the second end 119 along arrow 147, as shown in FIG. 11 and FIG. 12, locking mechanism 112 is in an unlocking state. In this state, the motion of second link 110 relative to first link 102 along first direction 111 occurs sustainably without impedance (no gas spring compression). In other words, when actuator 115 moves second end 119 along arrow 147, there will be no resistance for flexion of first link 102 and second link 110 relative to each other. In this situation, first link 102 and second link 110 are always free to extend relative to each other.

In some embodiments of the disclosure, actuator 115 comprises an element or combination of elements selected from a group consisting of electric motors, electric motors with transmission, solenoids, hydraulic actuators, pneumatic actuators and passive mechanical mechanisms.

Locking mechanism 112 represents the general mechanism that impeded the motion between the middle link 104 and the second link 110 when the locking mechanism 112 is in the locking state. In the embodiment of FIG. 8, locking mechanism 112 uses a wrap spring 117 and an arbor 109. In this embodiment, locking mechanism 112 is configured to impede the rotation of the second link 110 relative to the middle link 104 by use of the friction force between two surfaces. In this embodiment of the disclosure, where wrap spring 117 is used, in locking mechanism 112, a small actuator 115 can be employed to change the state of the locking mechanism 112. An ordinary skilled in the art would recognize that there are other methods of employing friction forces between surfaces to provide the intended function of locking mechanism 112. Examples of locking mechanism 112 include without limitation caliper brakes, disk brakes, band brake, ratchet and pawl assembly, linkage assemblies including bi-stable linkage assemblies.

Figure 13:
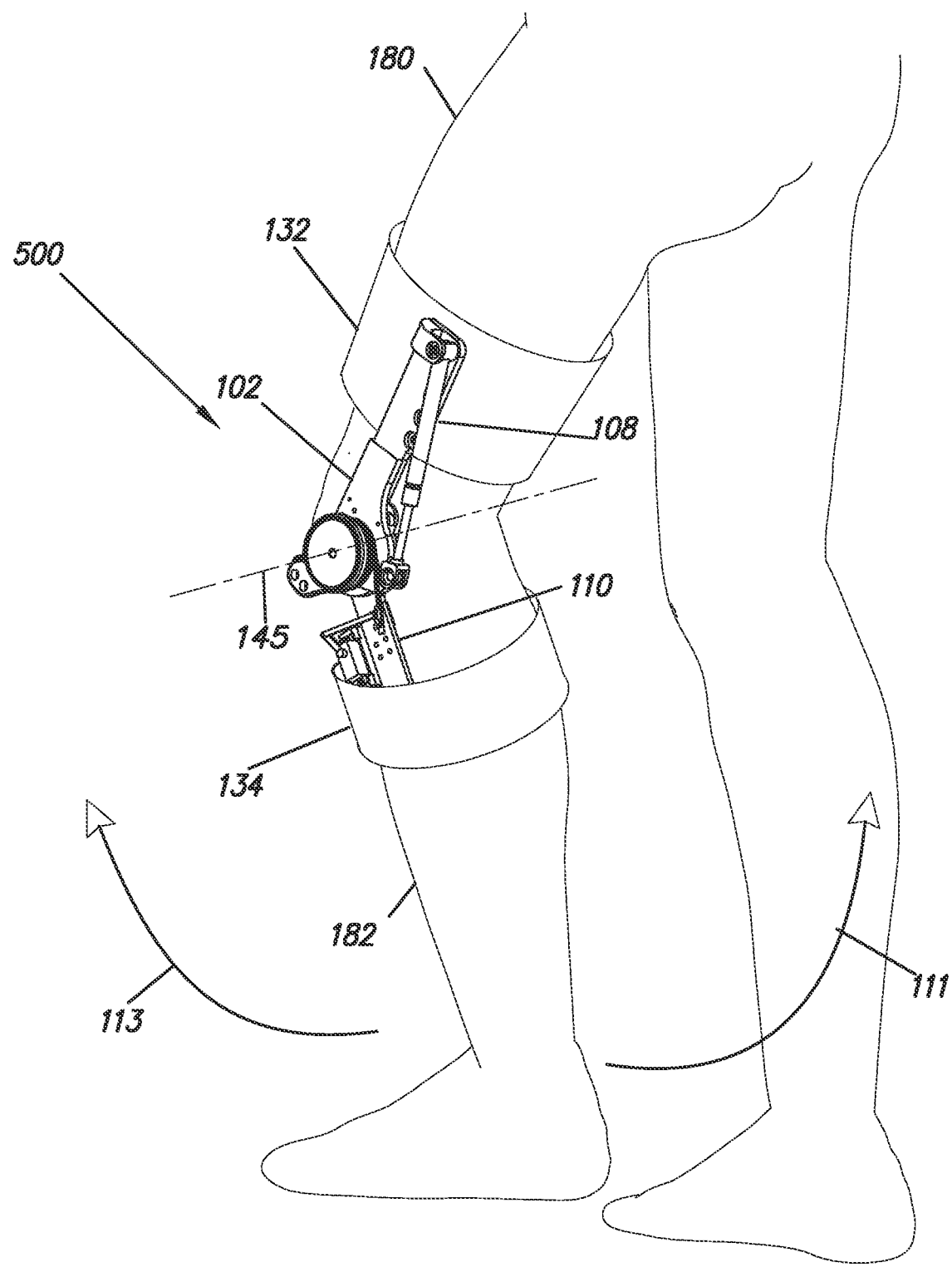
FIG. 13 illustrates an embodiment of an orthotic exoskeleton comprising an embodiment of a robotic joint.

FIG. 13 shows an embodiment of the disclosure where robotic joint 500 is coupled to a person's knee where first link 102 is coupled to a person's thigh 180 and second link 110 is coupled to person's shank 182. First direction 111 represents the knee flexion motion and second direction 113 is the knee extension motion. The person's knee joint is substantially coincident with the single axis of rotation 145 of robotic joint 500.

As shown in FIG. 13, in some embodiments of the disclosure, robotic joint 500 is coupled to a person's knee where first link 102 is configured to move in unison with person's thigh 180 and second link 110 is configured to move in unison with said person's shank 182. In some embodiments of the disclosure, robotic joint 500 further comprises a thigh connector 132 that allows coupling to a person's thigh 180. In some embodiments of the disclosure, robotic joint 500 further comprises a shank connector 134 that allows coupling to a person's shank 182. In some embodiments of the disclosures thigh connector 132 and shank connector 134 comprise braces. Although braces have been used to demonstrate the coupling of first link 102 and second link 110 to the person's thigh 180 and shank 182 in FIG. 13, an ordinary person skilled in the art would understand that many methods and devices can be employed that would cause second link 110 and first link 102 to move in unison with person's shank 182 and person's thigh 180. Coupling through shank braces and thigh braces is only one method of causing the unison movement of first link 102 with person's thigh 180 and second link 110 with wearer's shank 182.

Figure 14:
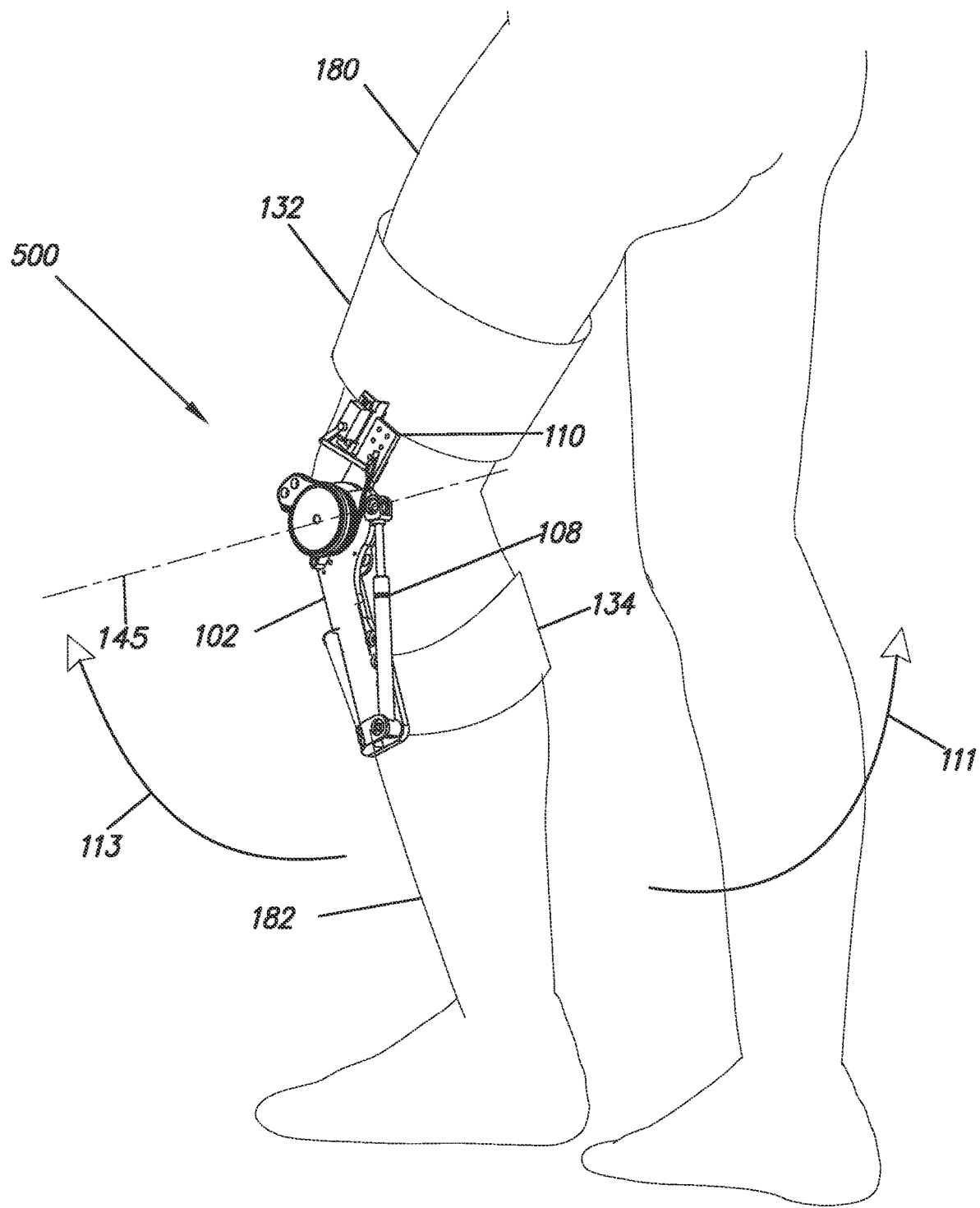
FIG. 14 illustrates an embodiment of an orthotic exoskeleton comprising an embodiment of a robotic joint.

FIG. 14 shows an embodiment where robotic joint 500 is employed in a manner mirrored to how it is used in FIG. 13. FIG. 14 shows an embodiment of the disclosure where robotic joint 500 is coupled to a person's knee where first link 102 is coupled to a person's shank 182 and second link 110 is coupled to the person's thigh 180. In some embodiments of the disclosure, robotic joint 500 is coupled to a person's knee where first link 102 is configured to move in unison with person's shank 182 and said second link 110 is configured to move in unison with said person's thigh 180 wherein first direction 111 is the knee flexion direction and second direction 113 is the knee extension direction. An ordinary person skilled in the art can see that mirroring the orientation of the embodiment in FIG. 13 produces the embodiment in FIG. 14. Thus, all description, which refers to the orientation of the embodiment shown in FIG. 13, can be applied to the orientation shown in FIG. 14.

Figure 15:
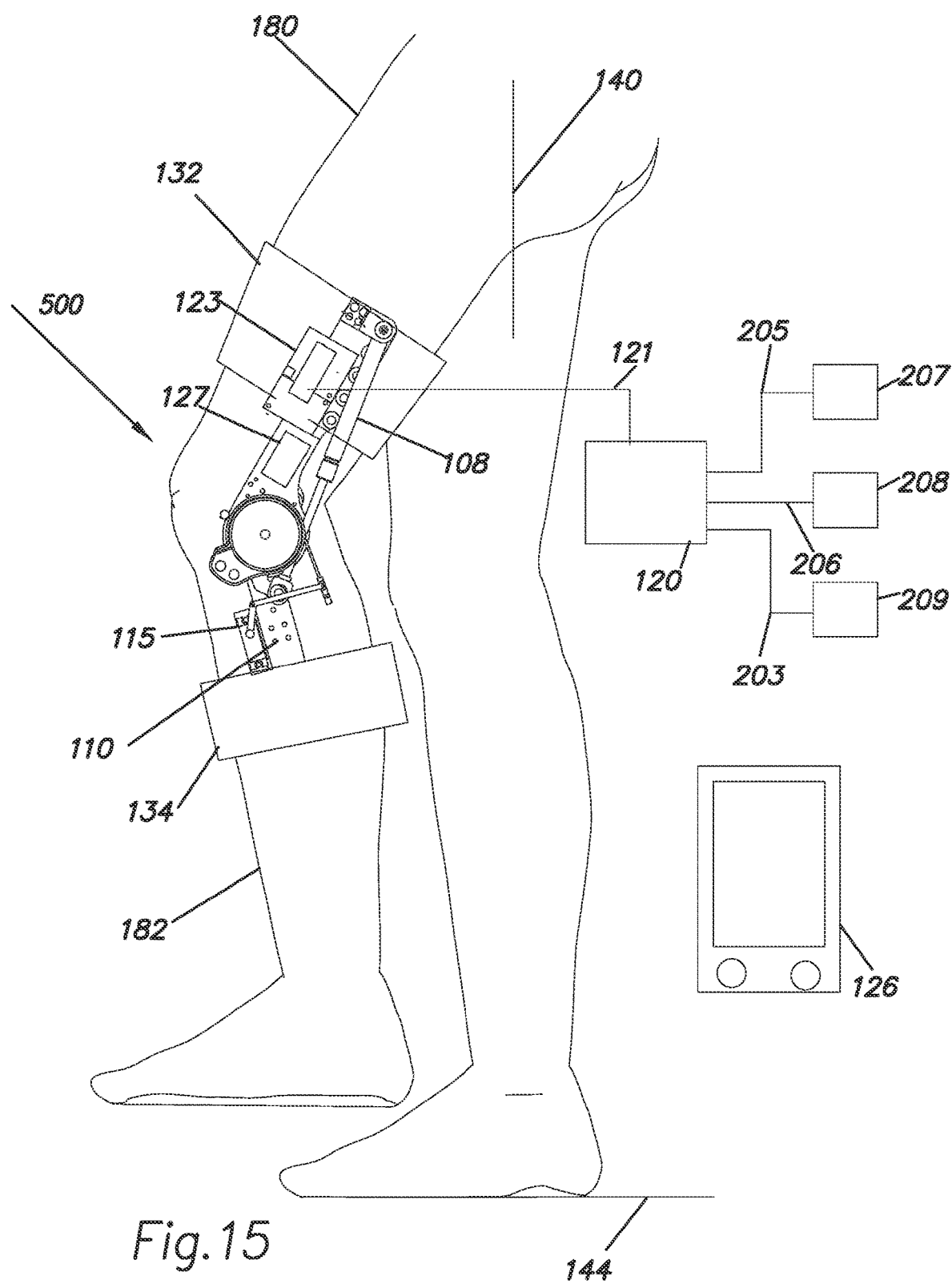
FIG. 15 illustrates an embodiment of an orthotic exoskeleton comprising an embodiment of a robotic joint.

FIG. 15 shows an embodiment of robotic joint 500, which is configured to be coupled to the lower extremity of a person. Robotic joint 500 further comprises a controller 120 (shown in FIG. 5) and at least one leg sensor 123 capable of producing a leg signal 121. Leg signal 121 is used by controller 120 to control the locking and unlocking states of locking mechanism 112. Examples of leg sensor 123 include, without limitation, rotary potentiometers, linear potentiometers, magnetic encoders, optical encoders, linear variable differential transformers, capacitive displacement sensors, eddy current proximity sensors, variable-inductance proximity sensors, rocker switches, slide switches, accelerometer, inertial measurement units, gyroscopes and combinations thereof.

Figure 21:
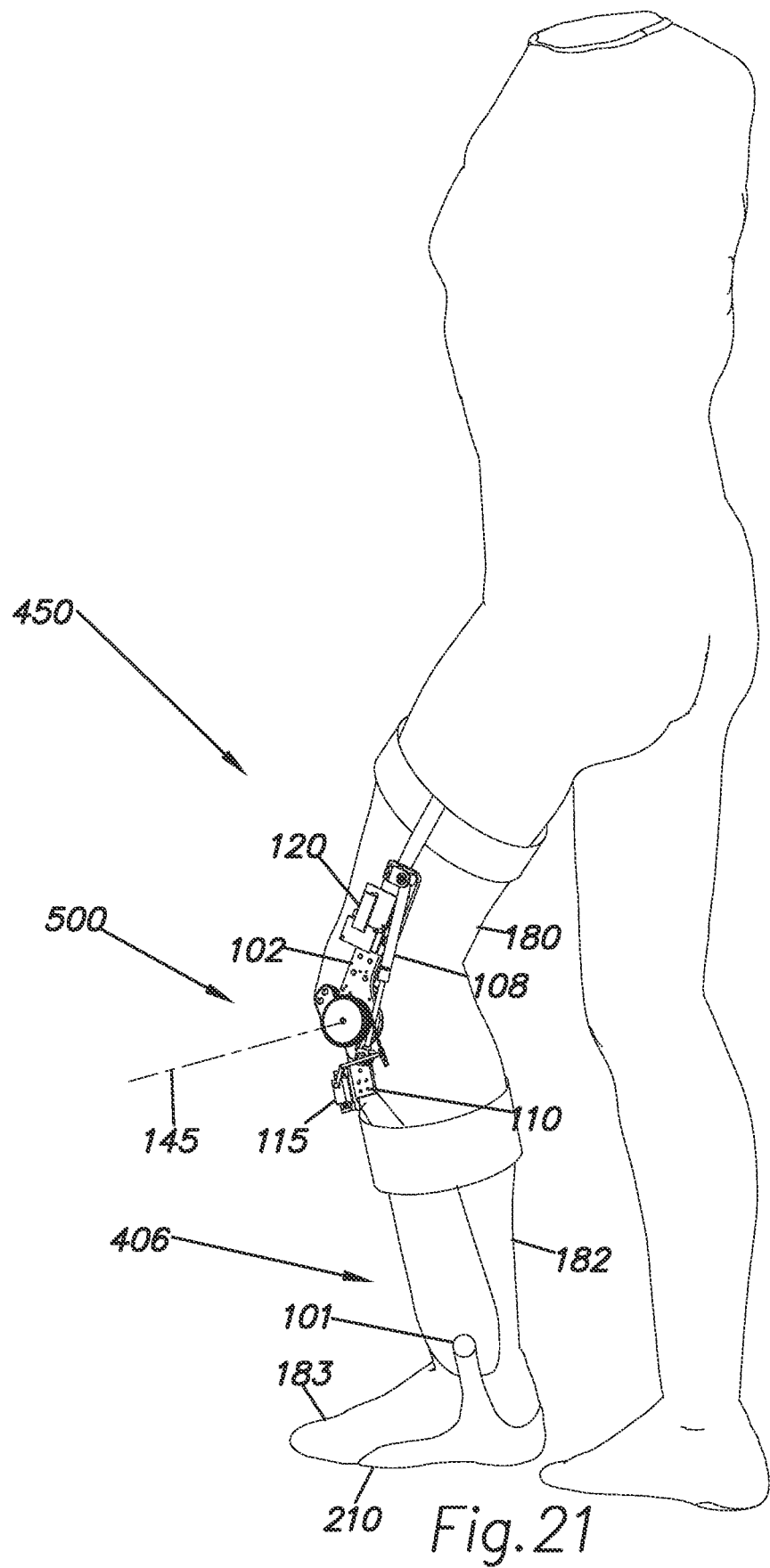
FIG. 21 illustrates an embodiment of an orthotic exoskeleton comprising an embodiment of a robotic joint.

Examples of leg signal 121 include, without limitation, a signal representing the absolute angle of the link coupled to person's thigh 180, which in some embodiments is first link 102 and in other embodiments is second link 110, relative to vertical gravitational line 140 or ground 144, a signal representing the velocity of the link coupled to person's thigh 180 relative to ground 144 or gravitational line 140, a signal representing the velocity of the link coupled to person's thigh 180, a signal representing the acceleration of link coupled to person's thigh 180 relative to ground 144 or gravitational line 140, a signal representing the angle between the person's torso 181 (person's torso is shown in FIG. 21) and the link coupled to the thigh 180, a signal representing the speed of the link coupled to the thigh 180 relative to the person's torso 181, a signal representing the acceleration of the link coupled to the thigh 180 relative to person's torso 181 and combinations thereof. In some embodiments of the disclosure, controller 120 is coupled to first link 102. In some embodiments of the disclosure, controller 120 is coupled to second link 110. In an embodiment of robotic joint 500, leg signal 121 is a signal that represents the absolute angle of first link 102 relative to vertical gravitational line 140 as shown in FIG. 15. In some embodiments, leg signal 121 indicates that the absolute angle of person's thigh 180 with respect to a line selected from the group consisting of vertical gravitational line 140 and a line substantially parallel with a person's torso. In some embodiments, leg signal 121 indicates that the absolute angle of one of first link 102 or second link 110, which is coupled to the person's thigh 180 with respect to a line selected from the group consisting of a vertical gravitational line 140 and a line substantially parallel with a person's torso.

Vertical gravitational line 140 is parallel to gravitational force. In the embodiment of FIG. 15, an inertial measurement unit (IMU) sensor can be secured to the person's thigh 180 and generates the absolute angle of the person's thigh 180 or the link coupled to the thigh (first link 102 in the embodiment shown in FIG. 13 or second link 110 shown in FIG. 14) with respect to vertical gravitational line 140. Since the person's thigh 180 and first link 102 move in unison with each other, then leg sensor 123 can be secured to either the person's thigh 180 or to first link 102.

Figure 16:
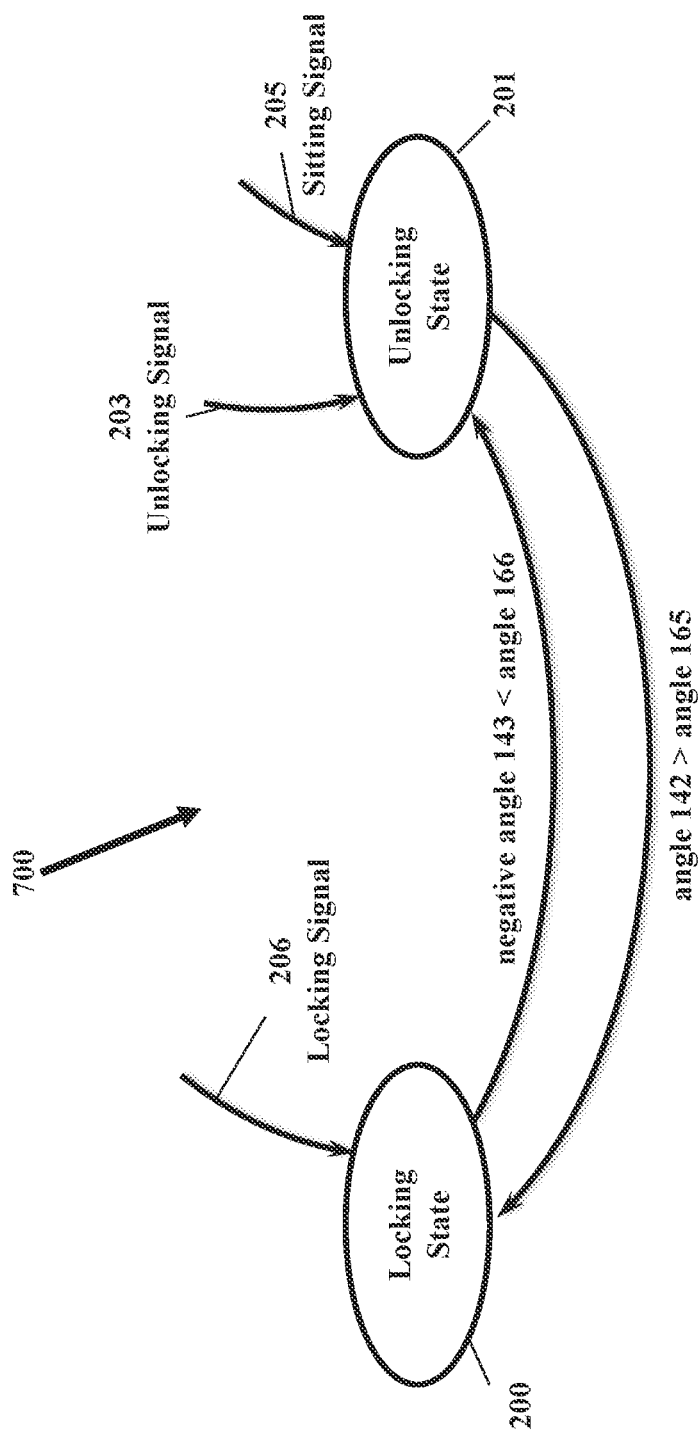
FIG. 16 illustrates an embodiment of the controller state machines.

FIG. 16 is a schematic illustration of controller finite state machine 700 having two primary states, in accordance with some embodiments. These states may include locking state 200 and unlocking state 201. Unlocking state 201 represents the state where locking mechanism 112 is in its unlocking state and first link 102 and second link 110 are free during both extension and flexion relative to each other. Locking state 200 represents the state where locking mechanism 112 is in its locking state where the flexion of first link 102 and second link 110 is impeded by torque generator 108.

Figure 17:
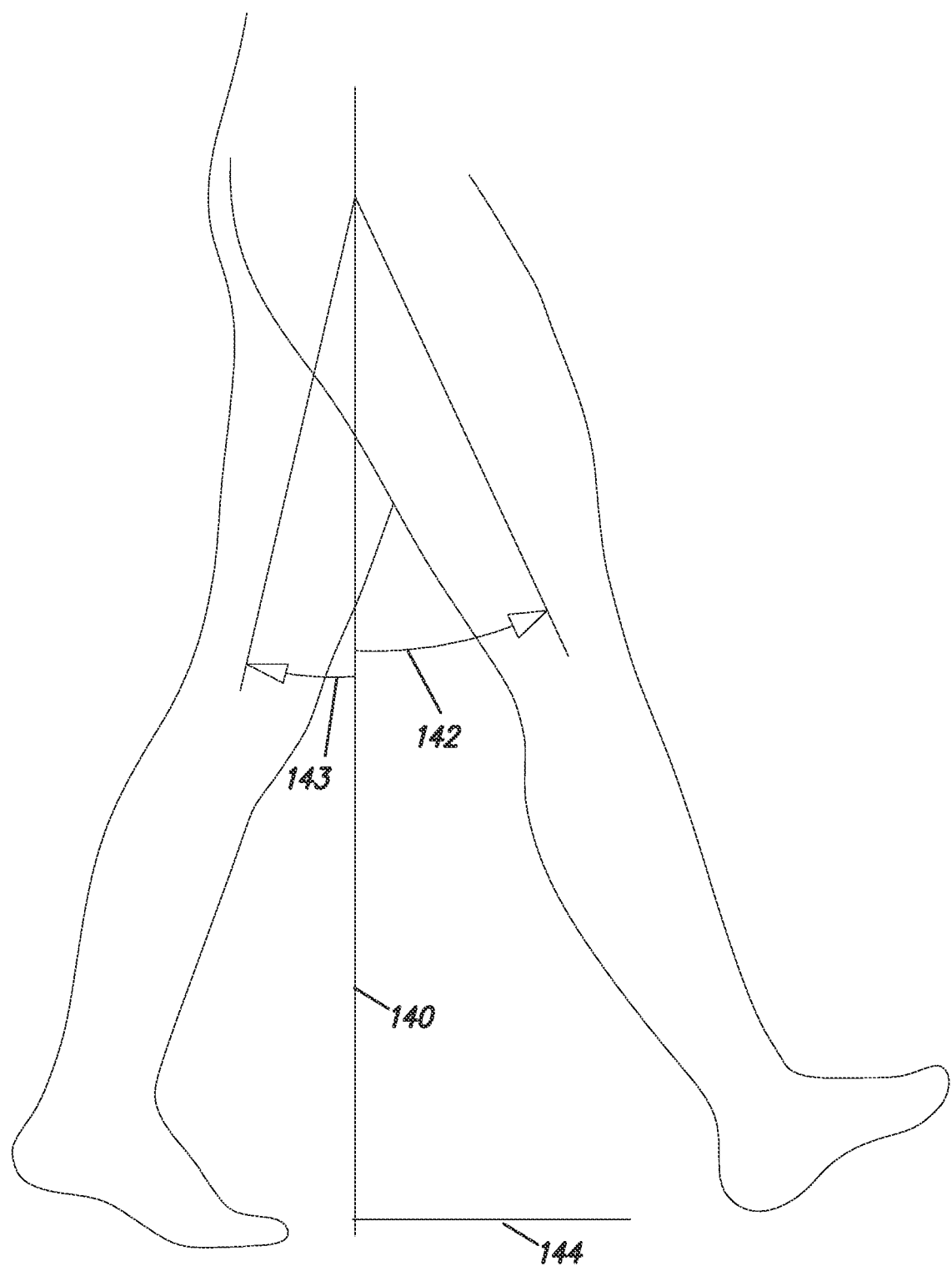
FIG. 17 illustrates the angles of wearers' thighs.
Figure 18:
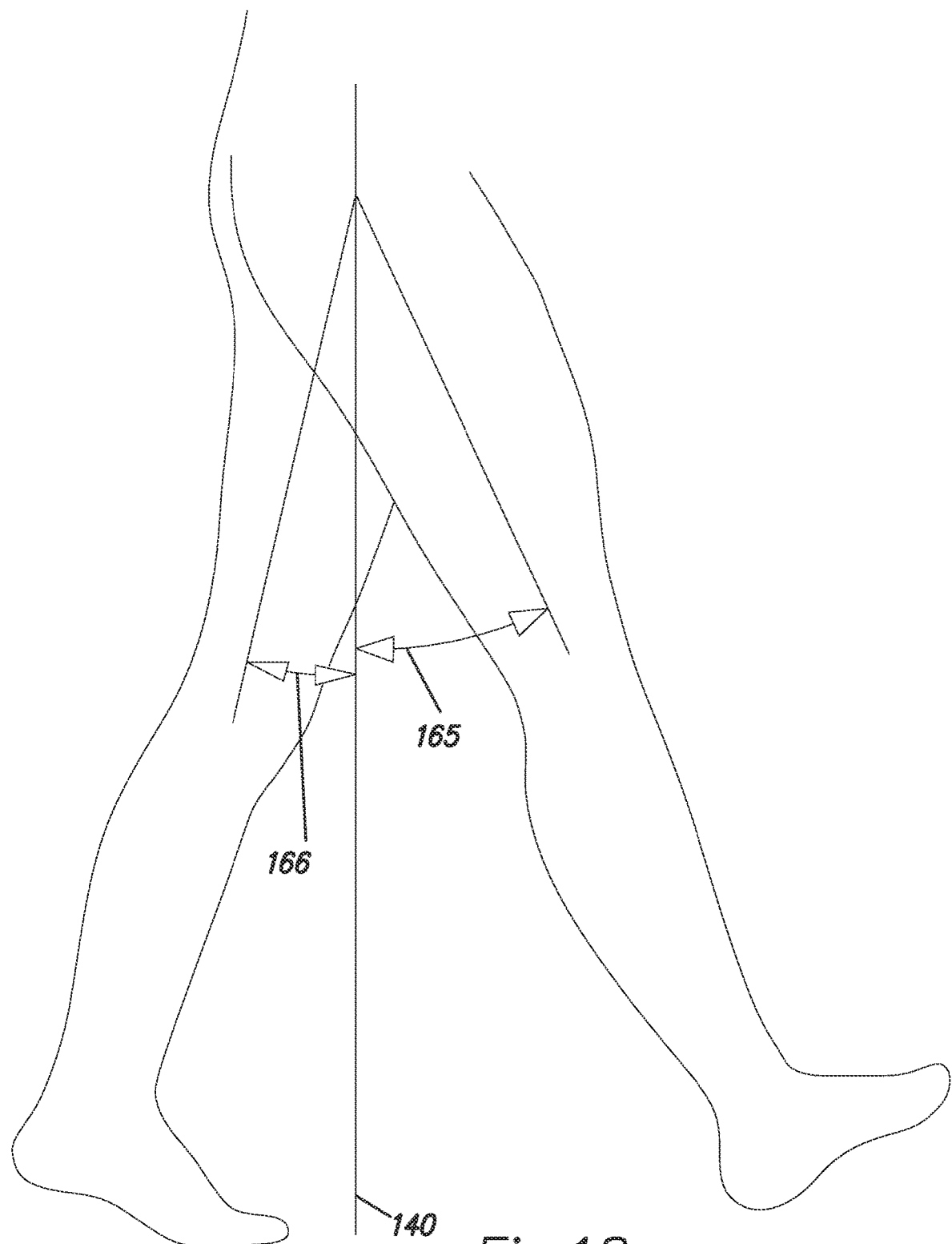
FIG. 18 illustrates the pre-specified maximum positive thigh angle and pre-specified minimum negative thigh angle.

In some embodiments, controller 120 may initially be in locking state 200. In locking state 200, controller 120 may enter unlocking state 201 if leg signal 121 is represented by, negative thigh angle 143 (FIG. 17), which is a signal representing the absolute angle of the person's thigh or the link coupled to person's thigh 180, (either first link 102 or second link 110), relative to vertical gravitational line 140, is smaller than a predefined minimum negative thigh angle 166. Predefined minimum negative thigh angle 166 is shown in FIG. 18. This means if robotic joint 500 is in its locking state (i.e., locking mechanism 112 is in its locking state), and if the measurement of the negative thigh angle 143 becomes smaller than the predefined minimum negative thigh angle 166, then finite state machine 700 will move to unlocking state 201. In this case, locking mechanism 112 moves into its unlocking state 201 and allows second link 110 to freely flex and extend relative to first link 102.

In some embodiments, when controller 120 is in unlocking state 201, controller 120 will enter locking state 200 if leg signal 121, represented by positive thigh angle 142 (FIG. 17), becomes larger than predetermined maximum positive thigh angle 165. Predetermined maximum positive thigh angle 165 is shown in FIG. 18. This means when the wearer leg is in the swing phase and the positive thigh angle from vertical 142 becomes larger than predetermined maximum positive thigh angle 165, locking mechanism 112 will move into locking state 200. In this situation, robotic joint 500 of FIG. 15 can freely extend, but torque generator 108 will provide resistance for flexion of first link 102 and second link 110 relative to each other. This resistance prevents robotic joint 500 from collapsing and supports the wearer's leg during the stance phase of the walking.

The controller can move to unlocking state 201 and locking state 200 as a result of external inputs also, which may be different from leg signal 121 generated by leg sensor 123.

In some embodiments, robotic joint 100 or 500 comprises manual locking device 208 as, for example, shown in FIG. 13. Manual locking device 208 is configured to generate locking signal 206 for controller 120. When manual locking device 208 is activated during operation and controller 120 receives locking signal 206, finite state controller moves into locking state 200. As noted above, in locking state 200, locking mechanism 112 is in its locking state, and the flexion motion of first link 102 and second link 110 is resisted by torque generator 108. In this case, the extension motion of first link 102 relative to second link 110 is free and unimpeded. In some embodiments of the disclosure, depending on the nature of the torque generator 108, the extension motion of first link 102 relative to second link 110 may be assisted.

In some embodiments, robotic joint 100 or 500 comprises manual unlocking device 209 as, for example, shown in FIG. 13. Manual unlocking device 209 is configured to generate manual unlocking signal 203 for controller 120. When manual unlocking device 209 is activated and controller 120 receives manual unlocking signal 203, robotic joint 100 or 500 moves into unlocking state 201. In unlocking state 201, locking mechanism 112 is in its unlocking state and first link 102 and second link 110 are free to flex and extend relative to each other.

In some embodiments of the disclosure, robotic joint 100 or 500 comprises manual sitting device 207. Manual sitting device 207 is configured to generate sitting signal 205 for controller 120. In operation, when sitting device 207 is activated and controller 120 receives sitting signal 205, robotic joint 100 or will move into unlocking state 201. This allows the wearer to comfortably sit on a chair without any resistance.

In some embodiments, as shown in FIG. 15, predetermined minimum negative thigh angle 166 and predetermined maximum positive thigh angle 165 are assigned to the controller 120 using a user interface 126. In some embodiments, user interface 126 is configured to display leg signal 121. In some embodiments, user interface 126 comprises any signal generator such as without limitation push buttons, switch, momentary switch, sliding switch, a knob, potentiometers, encoders, or combinations thereof. In some embodiments, the user interface 126 may comprise a graphical wearer interface. Some examples of graphical wearer interface 126 include, without limitation, a mobile phone, a tablet, a laptop, a desktop, a monitor, and combinations thereof. User interface 126 is configured to produce locking signal 206, unlocking signal 203, and sitting signal 205 and to transmit the signals (and other information) to controller 120.

Locking signal 206 is capable of moving the controller from any state to its locking state 200. Unlocking signal 203 is capable of moving the controller 120 from any state to the unlocking state 201. Sitting signal 205 is capable of moving the controller 120 from any state to the locking state 200. In some embodiments, the user interface 126 communicated with the controller 120 wirelessly via a wireless protocol. In some embodiments, the user interface 126 communicates with the controller 120 over wires.

Figure 19:
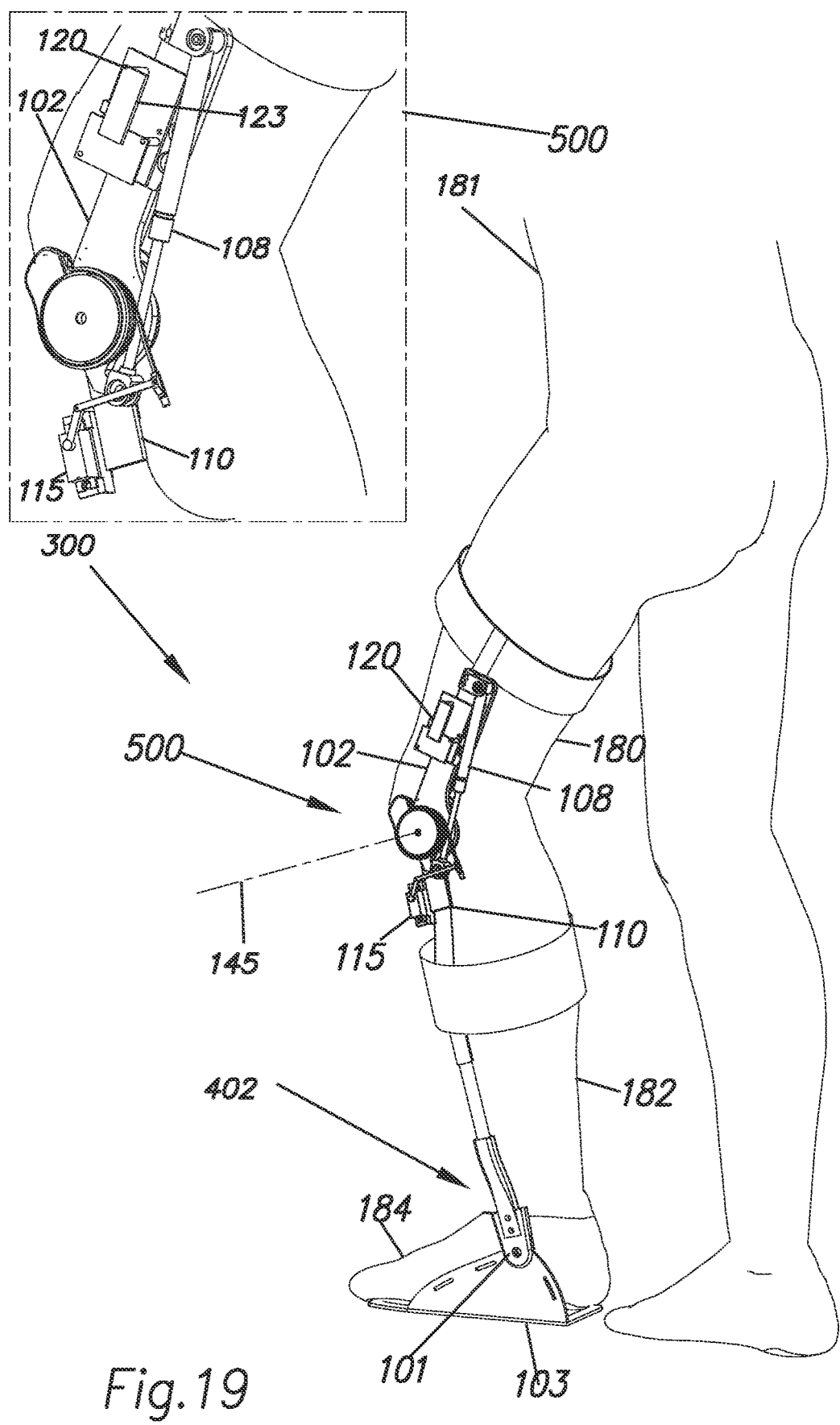
FIG. 19 illustrates an embodiment of an orthotic exoskeleton comprising an embodiment of a robotic joint.

Robotic joint 100 or 500 can be used in a variety of configurations. FIG. 19 shows an embodiment of an exoskeleton 300 which comprises robotic joint 500. In the embodiment shown in FIG. 19, first link 102 is coupled to a person's thigh 180 and second link 110 is coupled to person's shank 182. The person's knee joint is substantially aligned with a single axis of rotation 145. Second link 110 extends towards the ground and is coupled to foot link 103 such that foot link 103 can rotate relative to second link 110 about ankle joint 101. In some embodiments of the disclosure, foot link 103 is coupled to person's foot 183. Foot link 103 is coupled to the wearer to move in unison with person's foot 183 by using various forms of strapping and bracing. In some embodiments of the disclosure, foot link 103 is embedded into shoe 184. In some embodiments of the disclosure, foot link 103 is worn outside the wearer's shoes. In some embodiments of the disclosure, foot link 103 is worn inside the wearer's shoes.

In some embodiments of the disclosure, such as the embodiment shown in FIG. 19, exoskeleton 300 comprises robotic joint 500 and an ankle exoskeleton 402 which is capable of being coupled to person's foot 183. In some embodiments of the disclosure, ankle exoskeleton 402 is connectable to second link 110. In some embodiments of the disclosure, as shown in FIG. 19, ankle exoskeleton 402, is worn outside the wearer's shoes 184.

Figure 20:
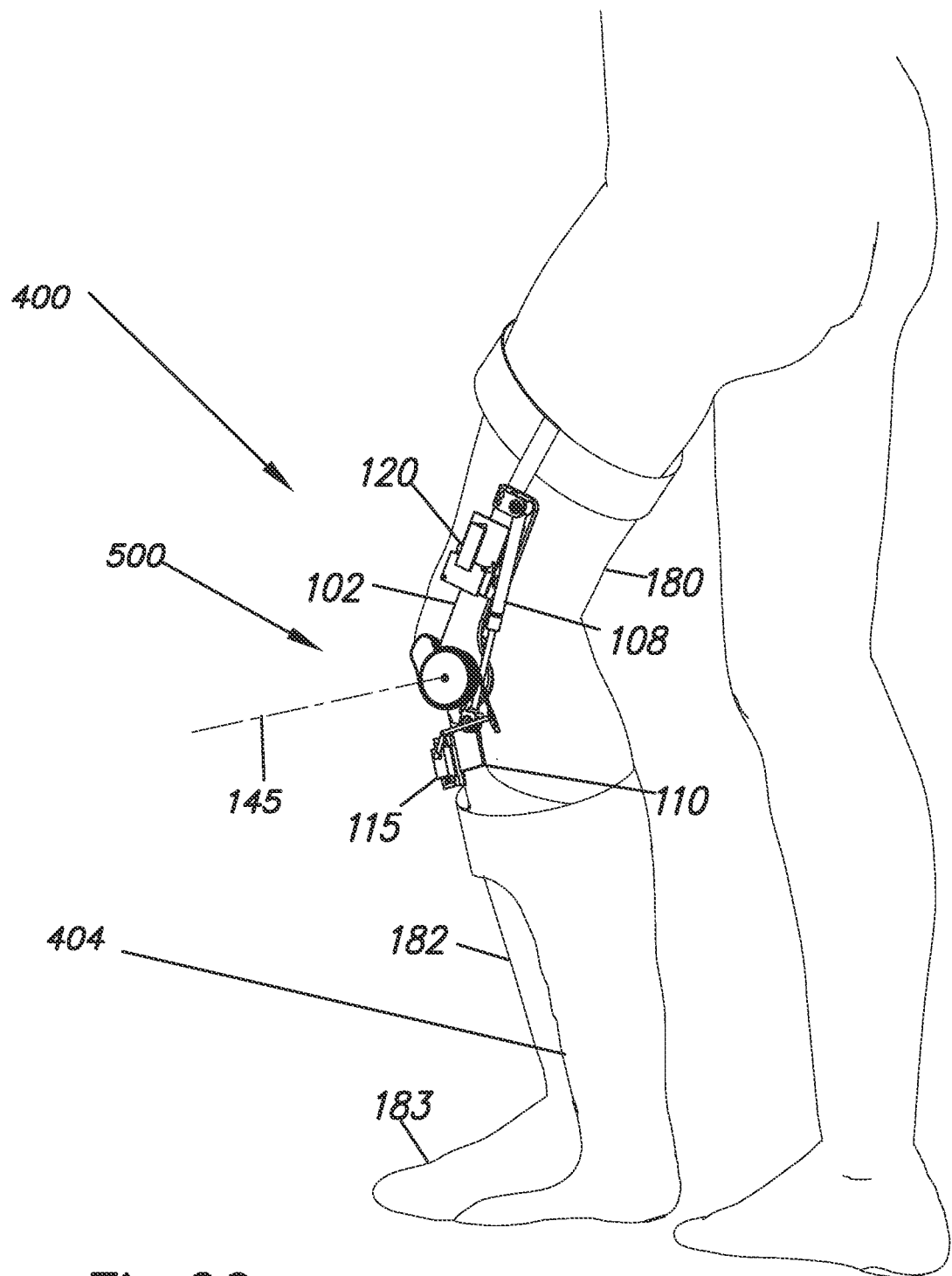
FIG. 20 illustrates an embodiment of an orthotic exoskeleton comprising an embodiment of a robotic joint.
Figure 22:
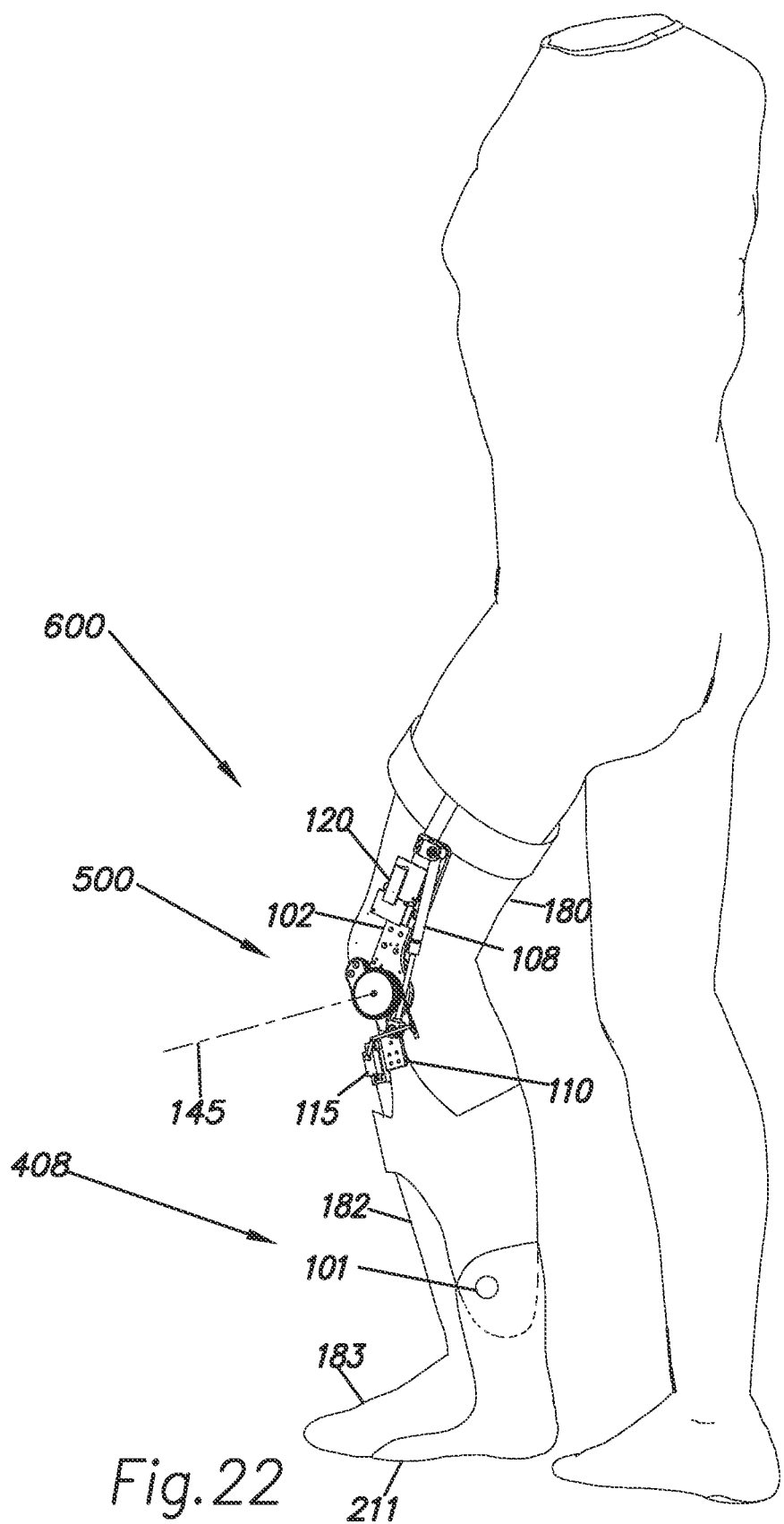
FIG. 22 illustrates an embodiment of an orthotic exoskeleton comprising an embodiment of a robotic joint.

FIGS. 20-22 depict embodiments of the disclosure wherein robotic joint 500 can be used in a variety of configurations in conjunction with various ankle-foot orthoses.

In some embodiments of the disclosure, as shown in FIG. 20, exoskeleton 400 comprises robotic joint 500 and ankle-foot-orthosis 404. In this embodiment ankle-foot-orthosis 404 is worn inside the wearer's shoe like an insole (the wearer's shoes are not shown for clarity). An ordinary person skilled in the art can arrive at many forms of internal and external ankle-foot-orthoses that can be used in conjunction with robotic joint 100 or 500.

FIG. 20 shows an embodiment of exoskeleton 400 where ankle-foot-orthosis 404 is a standard solid ankle-foot-orthosis. This type of ankle-foot-orthosis stops plantarflexion and also stops or limits dorsiflexion.

FIG. 21 shows an embodiment of exoskeleton 450 which comprises robotic joint 500 and ankle-foot-orthosis 406, which is a standard short leg ankle-foot-orthosis (AFO) with a fixed (but sometimes adjustable) hinge. This type of AFO is relatively light and easy to fit into shoes. Ankle foot orthosis 406 comprises foot link 210.

FIG. 22 shows exoskeleton 600 comprising robotic joint 500 and ankle-foot-orthosis 408, which is a Plantarflexion Stop AFO. This AFO acts to stop plantarflexion by not letting foot link 211 to point downwards. This type of AFO has an ankle joint 101 that allows for normal dorsiflexion of the foot.

It should be appreciated that, although specific examples of different ankle-foot orthosis are shown, there are other types of ankle-foot-orthosis that could be utilized with the present disclosure. For example, in some embodiments of the disclosure, ankle-foot-orthosis is a Dorsiflexion Assist AFO (not shown). This type of AFO is similar to the AFO shown in FIG. 21 but has a spring-like hinge that acts to raise the foot link when the foot comes off the ground. In some embodiments of the disclosure, the ankle-foot-orthosis is a standard Posterior Leaf Spring ankle-foot-orthosis. In some embodiments of the disclosure, the ankle-foot-orthosis is an Energy Return ankle-foot-orthosis. This type of AFO uses a natural flex built into the material of the AFO to provide assistance in dorsiflexion. These devices are often made of carbon graphite materials. In general, the ankle-foot-orthosis of the present disclosure comprises any device or combination of internal or external ankle-foot-orthosis capable of performing the indicated functions. Examples of external or internal ankle-foot-orthosis include, without limitation, flexible AFO, rigid AFO, AFO with tamarack flexure, AFO with anti-talus, AFO anti-talus (anterior shell or shell in the front), AFO with a free-motion ankle joint, AFO with an adjustable rigid ankle joint, AFO with a spring-loaded ankle joint, AFO with an adjustable spring-loaded ankle joint and combinations thereof.

Figure 23:
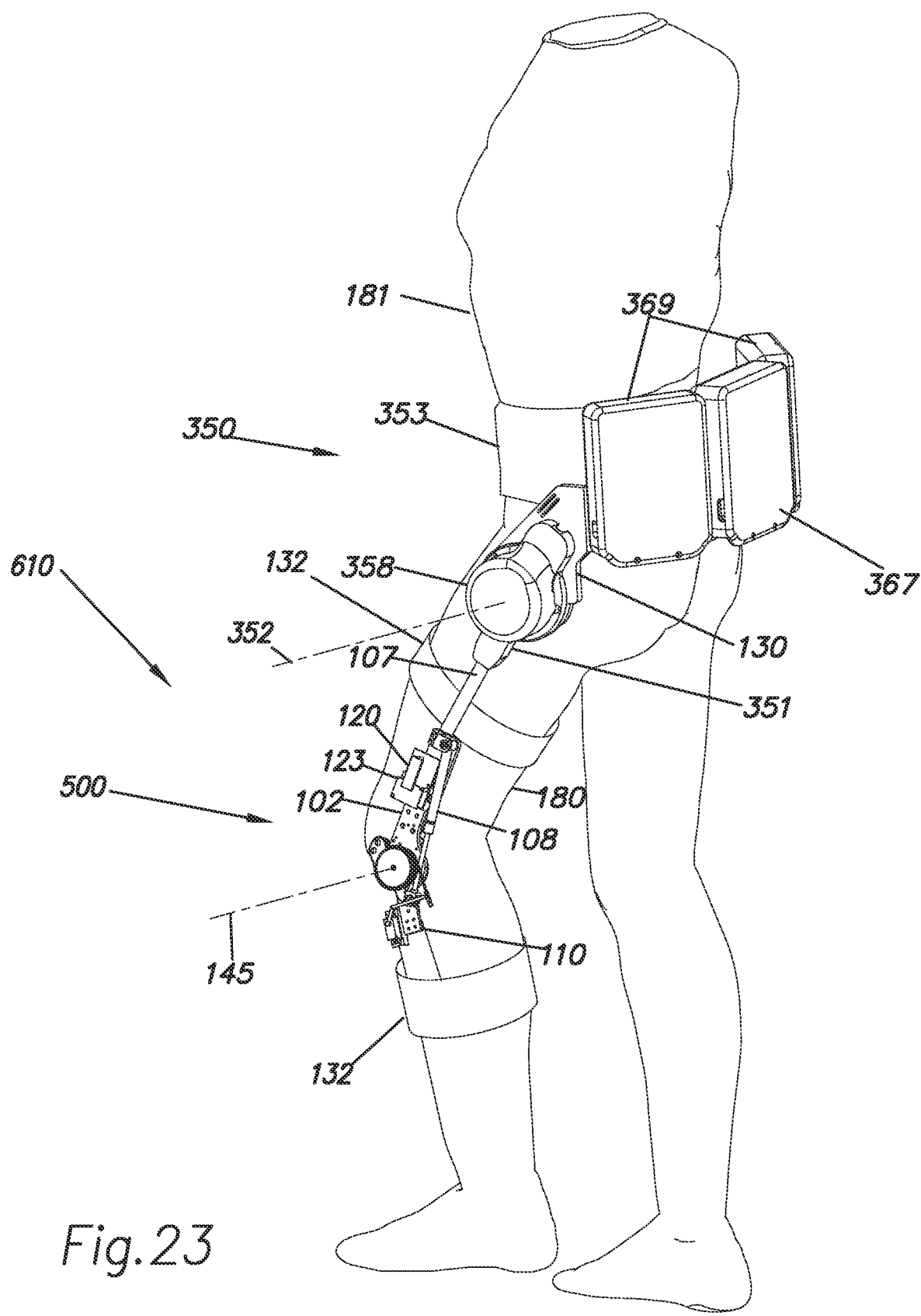
FIG. 23 illustrates an embodiment of an orthotic exoskeleton comprising an embodiment of a robotic joint.
Figure 24:
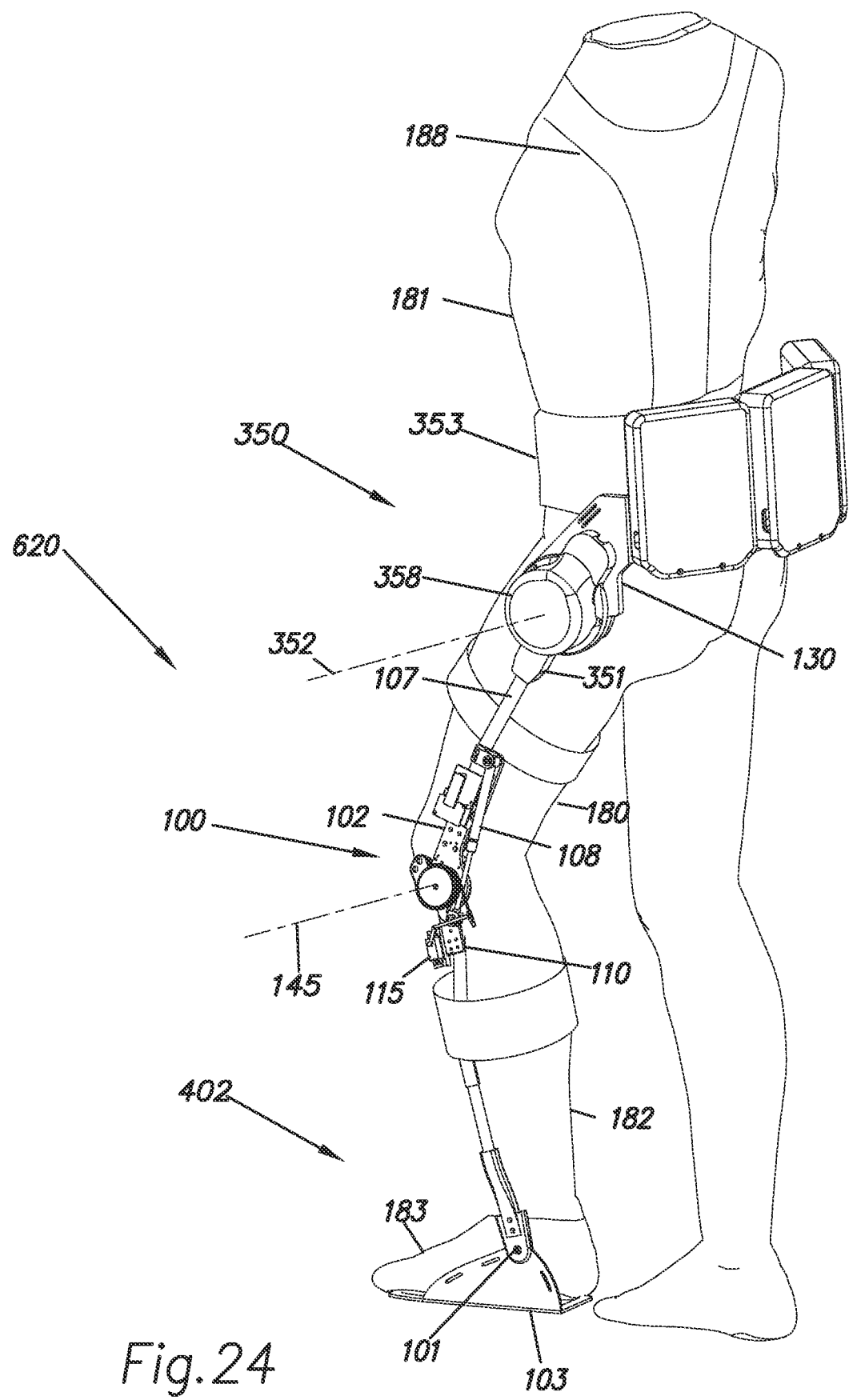
FIG. 24 illustrates an embodiment of an orthotic exoskeleton comprising an embodiment of a robotic joint.
Figure 25:
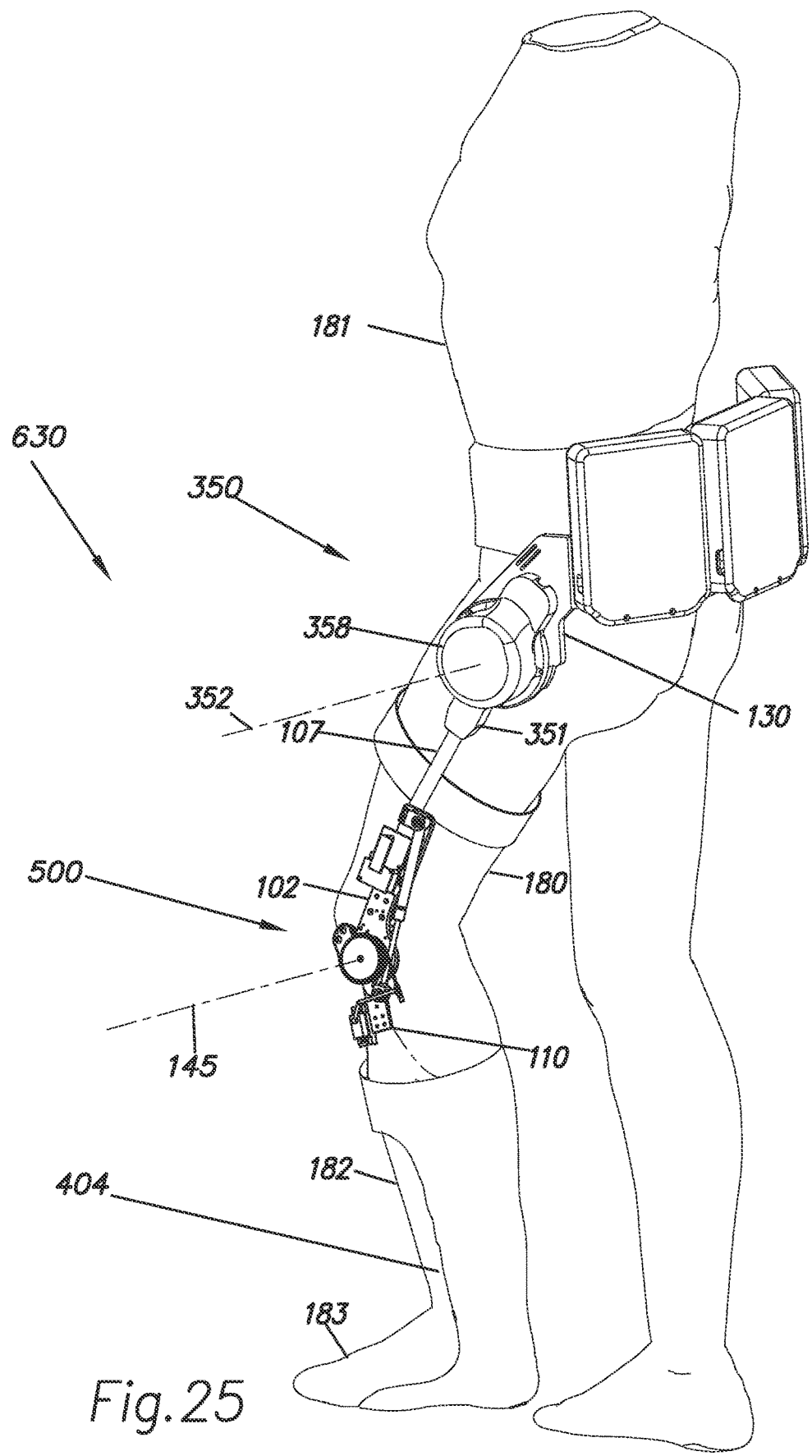
FIG. 25 illustrates an embodiment of an orthotic exoskeleton comprising an embodiment of a robotic joint.
Figure 26:
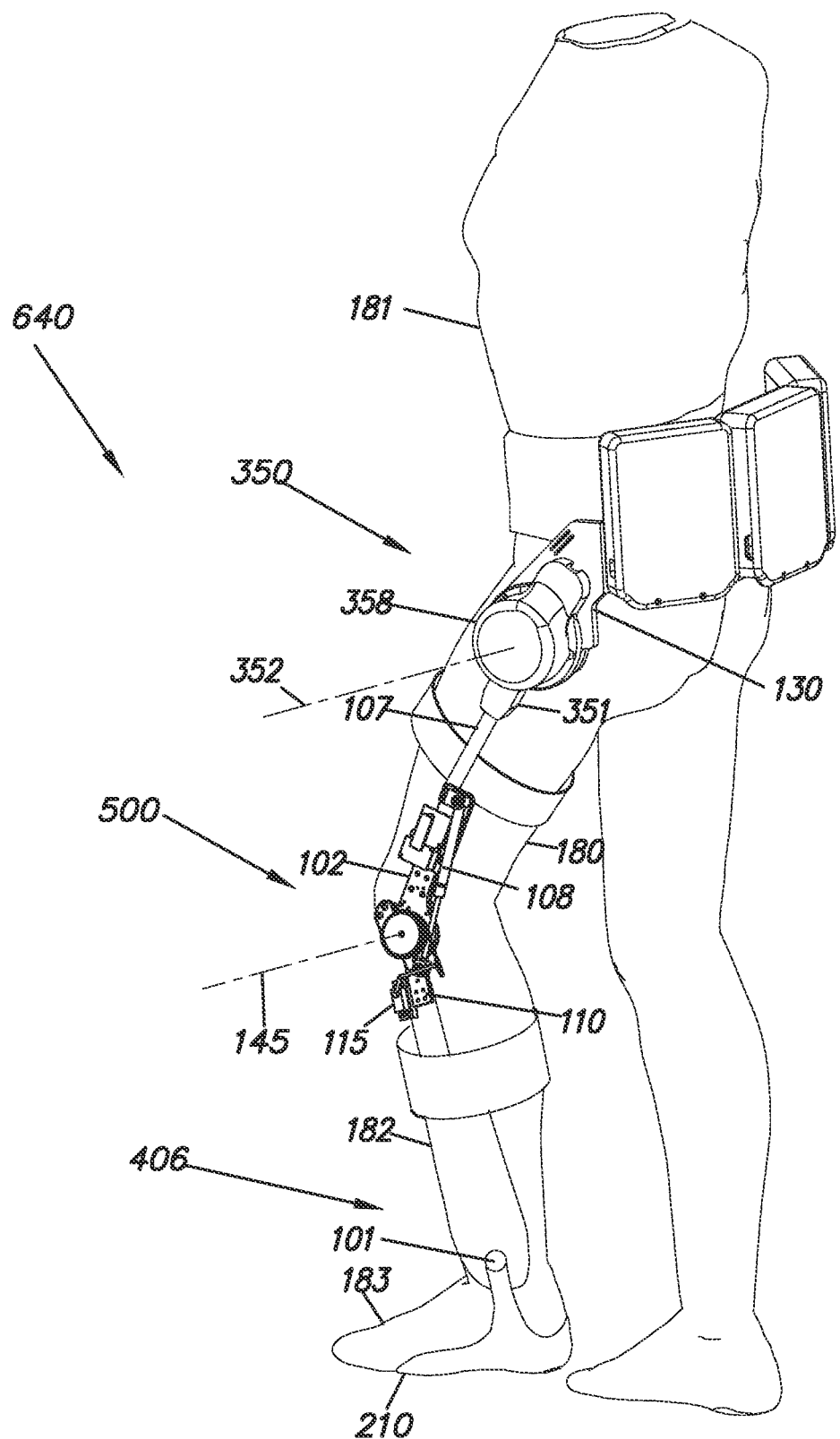
FIG. 26 illustrates an embodiment of an orthotic exoskeleton comprising an embodiment of a robotic joint.
Figure 27:
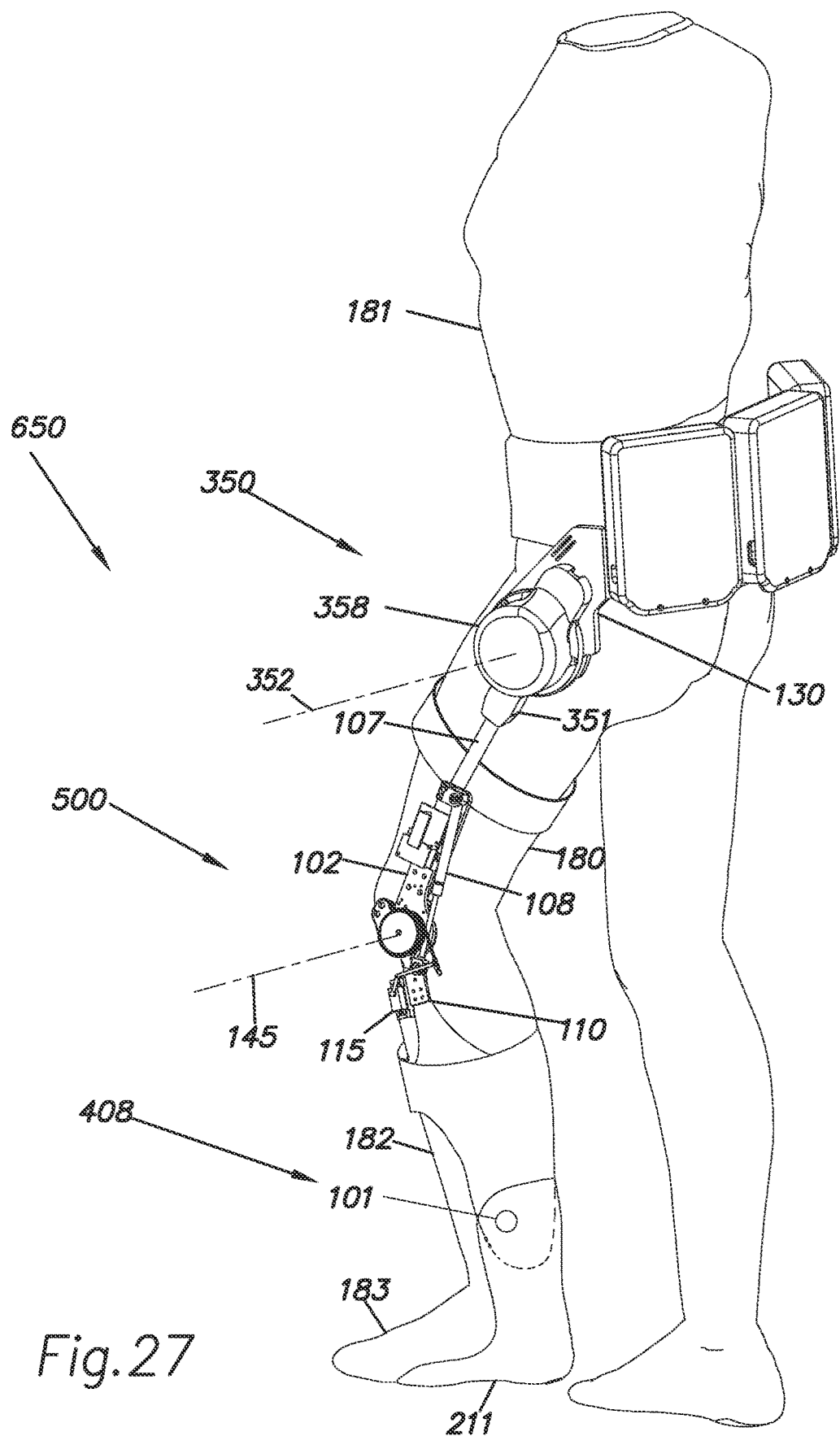
FIG. 27 illustrates an embodiment of an orthotic exoskeleton comprising an embodiment of a robotic joint.

FIG. 23 shows an embodiment of the disclosure where exoskeleton 610 further comprises an exoskeleton trunk 350. Exoskeleton trunk 350 is configurable to be coupled to the person's upper body 181. In some embodiments of the disclosure, exoskeleton trunk 350 couples torso link 130 coupled to the person's upper body 181 using a torso connection 353. In some embodiments of the disclosure, exoskeleton trunk 350 is coupled to a person like a backpack (not shown). In some embodiments of the disclosure, exoskeleton trunk 350 is coupled to a person like a belt, as depicted in FIG. 23, for example. Exoskeleton trunk 350 comprises a torso link 130 capable of being coupled to a person's upper body and torso. Exoskeleton trunk 350 further comprises thigh link 107 configured to be coupled to the person's thigh 180. Thigh link 107 is coupled to move in unison with the person's thigh 180. In some embodiments, thigh link 107 of exoskeleton trunk 350 is coupled to first link 102 of robotic joint 500. In some embodiments thigh link 107 of exoskeleton trunk 350 is coupled to second link 110 of robotic joint 500. In some embodiments of the disclosure exoskeleton trunk 350 and robotic joint 500 are not coupled together. Exoskeleton trunk 350 further comprises a trunk thigh link 351 configurable to rotatably couple thigh link 107 to torso link 130. In some embodiments of the disclosure, trunk thigh link 351 is coupled to thigh link 107. In some embodiments of the disclosure, trunk thigh link 351 is not coupled to thigh link 107. In an alternative embodiment not shown, trunk thigh link 351 is coupled to person's thigh 180. In some embodiments of the disclosure, exoskeleton trunk 350 further comprises an actuator 358 capable of providing torque between torso link 130 and trunk thigh link 351. Axis 352 is the hip flexion extension axis. The controller box 367 and the batteries 369 for the actuators are shown in FIG. 23. In some embodiments of the disclosure, leg signal 121 represents the absolute angle of first link 102 relative to a vertical gravitational line 140 or relative to ground 144. In some embodiments of the disclosure, leg signal 121 represents the absolute angle of trunk thigh link 351 relative to a vertical gravitational line 140 or relative to ground 144 (not shown). In some embodiments of the disclosure, leg signal 121 represents the angle of trunk thigh link 351 with respect to torso link 130 which is substantially parallel with the person's torso.

FIGS. 24-27 depict embodiments of the present disclosure (exoskeletons 620, 630, 640, and 650) including both an exoskeleton trunk 350 and an ankle exoskeleton or ankle-foot orthosis (e.g., 402, 404, 406, and 408). In the embodiments shown, the ankle-foot orthosis of the present disclosure (404, 406, 408) is capable of being coupled to person's foot 183 and is connectable to a link coupled to the shank 182 such as the second link 114. The embodiment of FIG. 24, exoskeleton trunk 350 is coupled to a person with shoulder straps 188.

What is claimed is:

1. A robotic exoskeleton joint configured to be coupled to a lower extremity of a person, the robotic exoskeleton joint comprising:
   a first link;
   a middle link, comprising a first end and a second end, wherein the first end of the middle link is rotatably coupled to the first link at a first joint;
   a torque generator, configured to produce a torque between the first link and the middle link;
   a second link, rotatably coupled to the second end of the middle link at a second joint; and
   a locking mechanism, switchable between a locking state and an unlocking state independent of the torque of the torque generator, wherein:
      the locking mechanism, in the locking state, prevents flexion of the second link and the middle link relative to each other,
      the locking mechanism, in the unlocking state, allows free flexion and extension of the second link and the middle link relative to each other, and
      when the locking mechanism is in the locking state and thereby prevents the flexion of the second link and the middle link relative to each other, the torque generator impedes flexion of the second link and the first link about the first joint by applying torque to the middle link.

2. The robotic exoskeleton joint of claim 1, wherein an axis of rotation of the first link relative to the middle link and an axis of rotation of the second link relative to the middle link coincide with each other.

3. The robotic exoskeleton joint of claim 1, wherein an axis of rotation of the first link relative to the middle link and an axis of rotation of the second link relative to the middle link are substantially parallel to each other.

4. The robotic exoskeleton joint of claim 1, further comprising an actuator, wherein the locking mechanism locks the middle link to the second link by the actuator.

5. The robotic exoskeleton joint of claim 4, wherein the actuator comprises an element or a combination of elements selected from the group consisting of an electric motor, an electric motor with a transmission, a solenoid, a hydraulic actuator, and a pneumatic actuator.

6. The robotic exoskeleton joint of claim 1, wherein the torque generator is selected from the group consisting of a pneumatic cylinder, a hydraulic cylinder, a cylinder with a hydraulic component, a cylinder with a pneumatic component, a gas spring, an air spring, a hydraulic damper, a lockable gas spring, a lockable damper, a compression spring, a tensile spring, a coil spring, an electric motor, an electric motors with a transmission, a solenoid, a hydraulic actuator, and a pneumatic actuator.

7. The robotic exoskeleton joint of claim 1,
   wherein one of the first link and the second link is configurable to be coupled to a thigh of the person, and
   wherein another one of the first link and the second link is configurable to be coupled to a shank of the person.

8. The robotic exoskeleton joint of claim 1, wherein one of the first link and the second link is configurable to move in unison with a thigh of a person, wherein another one of the first link and the second link is configurable to move in unison with a shank of the person.

9. The robotic exoskeleton joint of claim 1, further comprising at least one controller configured to move the locking mechanism to the locking state just before a leg of the person strikes a ground.

10. The robotic exoskeleton joint of claim 1, further comprising at least one controller configured to move the locking mechanism to the unlocking state just before a stance phase is over.

11. The robotic exoskeleton joint of claim 1, further comprising at least one controller operable to receive at least one leg signal from the robotic exoskeleton joint, wherein the controller is configured to move the locking mechanism to the locking state based on the at least one leg signal.

12. The robotic exoskeleton joint of claim 11, wherein the at least one signal represents an absolute angle of one of the first link or the second link, which is configured to be coupled to a thigh of the person, with respect to a line selected from the group consisting of a vertical gravitational line and a line substantially parallel with a torso of the person.

13. The robotic exoskeleton joint of claim 11, wherein the at least one signal represents an absolute angle of a thigh of the person with respect to a line selected from the group consisting of a vertical gravitational line and a line substantially parallel with a torso of the person.

14. The robotic exoskeleton joint of claim 11, wherein the at least one controller is configured to move the locking mechanism to the locking state when the at least one leg signal indicates that an absolute angle of a thigh of the person with respect to a line selected from the group consisting of a vertical gravitational line and a line substantially parallel with a torso of the person is larger than a pre-specified maximum positive thigh angle.

15. The robotic exoskeleton joint of claim 11, wherein the at least one controller is configured to move the locking mechanism into an unlocking state when the at least one leg signal indicates that an absolute angle of a thigh of the person with respect to a line selected from the group consisting of a vertical gravitational line and a line substantially parallel with a torso of the person is smaller than a pre-specified minimum negative thigh angle.

16. The robotic exoskeleton joint of claim 11, wherein the at least one controller is configured to move the locking mechanism to the locking state when the at least one leg signal indicates that an absolute angle of the first link or the second link, which is configured to be coupled to a thigh of the person with respect to a line selected from the group consisting of a vertical gravitational line and a line substantially parallel with a torso of the person is larger than a pre-specified maximum positive thigh angle.

17. The robotic exoskeleton joint of claim 11, wherein the at least one controller is configured to move the locking mechanism into the unlocking state when the at least one leg signal indicates that an absolute angle of the first link or the second link, which is configured to be coupled to a thigh of a person, with respect to a line selected from the group consisting of a vertical gravitational line and a line substantially parallel with a torso of the person is smaller than a pre-specified minimum negative thigh angle.

18. The robotic exoskeleton joint of claim 11 further comprising a manual locking device operable to generate a manual locking signal for the at least one controller, wherein, when the manual locking signal is activated by the person, the locking mechanism moves into the locking state.

19. The robotic exoskeleton joint of claim 11, further comprising a manual unlocking device operable to generate a manual unlocking signal for the at least one controller, wherein, when the manual unlocking device is activated by the person, the locking mechanism moves into the unlocking state.

* * * * *

UNITED STATES PATENT AND TRADEMARK OFFICE
CERTIFICATE OF CORRECTION

PATENT NO. : 11,819,428 B2
APPLICATION NO. : 17/663610
DATED : November 21, 2023
INVENTOR(S) : Kazerooni et al.

It is certified that error appears in the above-identified patent and that said Letters Patent is hereby corrected as shown below:

In the Claims

In Column 14, Claim 8, Line 26, delete "a person," and replace with --the person--.

In Column 15, Claim 17, Line 17, delete "a person," and replace with --the person--.

Signed and Sealed this
Thirtieth Day of January, 2024

Katherine Kelly Vidal
*Director of the United States Patent and Trademark Office*